(12) United States Patent
Pesach et al.

(10) Patent No.: US 11,020,208 B2
(45) Date of Patent: Jun. 1, 2021

(54) SYSTEM, DEVICE, AND METHOD FOR INTRAORAL SCANNING ACCURACY

(71) Applicant: DENTLYTEC G.P.L. Ltd., Tel-Aviv (IL)

(72) Inventors: Benny Pesach, Rosh HaAyin (IL); Georgy Melamed, Ramat-Gan (IL); Blanc Zach Lehr, Tel-Aviv (IL); Ygael Grad, Tel-Aviv (IL)

(73) Assignee: DENTLYTEC G.P.L. LTD., Tel Aviv (IL)

( * ) Notice: Subject to any disclaimer, the term of this patent is extended or adjusted under 35 U.S.C. 154(b) by 0 days.

(21) Appl. No.: 15/542,395

(22) PCT Filed: Apr. 21, 2016

(86) PCT No.: PCT/IL2016/050023
§ 371 (c)(1),
(2) Date: Jul. 7, 2017

(87) PCT Pub. No.: WO2016/110855
PCT Pub. Date: Jul. 14, 2016

(65) Prior Publication Data
US 2018/0028292 A1    Feb. 1, 2018

Related U.S. Application Data

(60) Provisional application No. 62/100,920, filed on Jan. 8, 2015.

(51) Int. Cl.
*A61C 9/00*    (2006.01)
*A61B 1/24*    (2006.01)
*A61B 5/00*    (2006.01)

(52) U.S. Cl.
CPC .............. *A61C 9/0053* (2013.01); *A61B 1/24* (2013.01); *A61B 5/0088* (2013.01); *A61C 9/004* (2013.01)

(58) Field of Classification Search
CPC ..... A61C 9/0053; A61C 9/004; A61C 9/0046; A61C 13/0004; A61C 19/04;
(Continued)

(56) References Cited

U.S. PATENT DOCUMENTS 6,671,539 B2    12/2003 Gateno et al.
2008/0002869 A1    1/2008 Scharlack et al.
(Continued)

FOREIGN PATENT DOCUMENTS

DE    102013204207 A1    9/2014
WO    WO 2011/112454 A1    9/2011
(Continued)

OTHER PUBLICATIONS

Flugge, T. V. et al., "Precision of intraoral digital dental impressions with iTero and extraoral digitization with the Tero and a model scanner," American Journal of Orthodontics and Dentofacial Orthopedics, vol. 144, No. 3, pp. 471-478, Sep. 2013.
(Continued)

*Primary Examiner* — Jacqueline T Johanas
*Assistant Examiner* — Shannel Nicole Belk
(74) *Attorney, Agent, or Firm* — Cooley LLP

(57) ABSTRACT

Methods and devices are disclosed, by use of which an external fiducial element positioned in the mouth serves as a geometrical constraint on oral arch geometry. In some embodiments, the fiducial element is an oral insert which reaches to a plurality of oral arch regions to present surface details which are in well-defined distance and/or angular relationships to one another. These spatial relationships optionally comprise a spatial frame of reference which serves to constrain reconstruction of the geometry of one or both of the oral arches, for example reconstruction from a collection of digitally registered, partially-overlapping scans made along the oral arch.

16 Claims, 16 Drawing Sheets

(58) Field of Classification Search
CPC ....... A61C 19/045; A61C 1/084; A61C 7/002; A61B 5/0088; A61B 1/24
See application file for complete search history.

(56) References Cited

U.S. PATENT DOCUMENTS

| | | |
|---|---|---|
| 2009/0176182 A1 | 7/2009 | Carillo Fuentevilla |
| 2010/0019170 A1 | 1/2010 | Hart et al. |
| 2010/0268071 A1* | 10/2010 | Kim .................. A61C 19/04 600/426 |
| 2013/0273492 A1 | 10/2013 | Suttin, Sr. et al. |
| 2014/0170583 A1* | 6/2014 | Kuo .................... A61B 1/24 433/3 |
| 2014/0170587 A1 | 6/2014 | Kopelman |
| 2015/0118640 A1* | 4/2015 | Schmitt ............. A61C 19/045 433/37 |
| 2016/0008107 A1* | 1/2016 | Brunner ............. A61C 9/0006 433/41 |

FOREIGN PATENT DOCUMENTS

| | | |
|---|---|---|
| WO | WO 2014020247 A1 | 2/2014 |
| WO | WO 2016110855 A1 | 7/2016 |

OTHER PUBLICATIONS

Geng, J., "Structured-light 3D surface imaging: a tutorial," Advances in Optics and Photonics 3, pp. 128-160, 2011.
Maintz, J. B. A. et al., "A Survey of Medical Image Registration," Medical Image Analysis, vol. 2, No. 1, pp. 1-36 Mar. 1988.
International Preliminary Report on Patentability dated Jul. 20, 2017 From the International Bureau of WIPO Re. Application No. PCT/IL2016/050023. (10 Pages).
International Search Report and the Written Opinion dated Apr. 21, 2016 From the International Searching Authority Re. Application No. PCT/IL2016/050023.
Supplementary European Search Report and the European Search Opinion dated Jun. 28, 2018 From the European Patent Office Re. Application No. 16734969.5. (11 Pages).

* cited by examiner

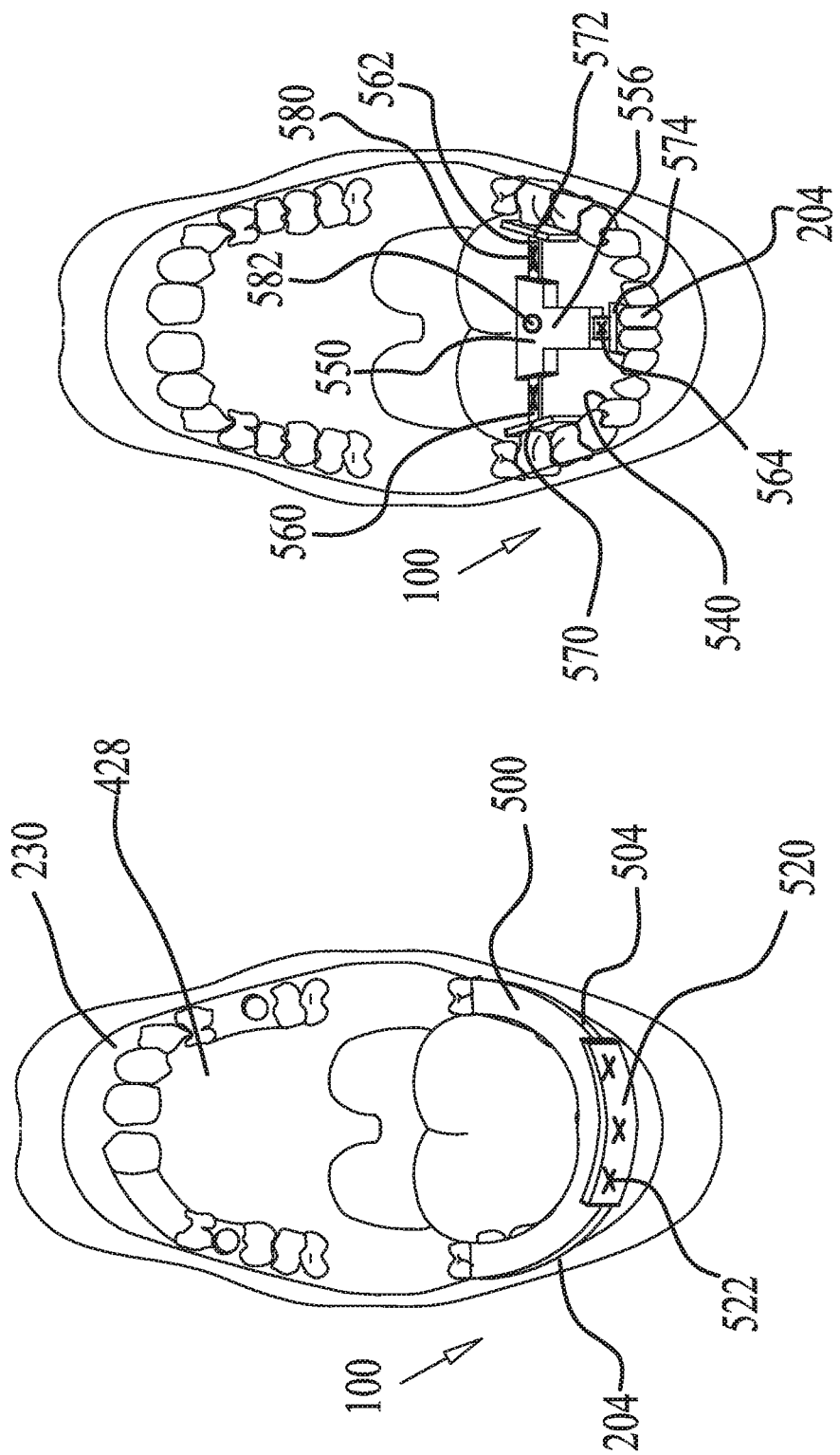

SYSTEM, DEVICE, AND METHOD FOR INTRAORAL SCANNING ACCURACY

RELATED APPLICATIONS

This application is a National Phase of PCT Patent Application No. PCT/IL2016/050023 having International filing date of Jan. 7, 2016, which claims the benefit of priority under 35 USC § 119(e) of U.S. Provisional Patent Application No. 62/100,920 filed on Jan. 8, 2015. The contents of the above applications are all incorporated by reference as if fully set forth herein in their entirety.

FIELD AND BACKGROUND OF THE INVENTION

This disclosure relates to dental scanning techniques, and specifically to systems, devices and methods for accurate intraoral scanning of a full or partial arch.

Dental restorations may include full or partial arch restorations. Some cases may also include partially or full edentulous conditions, wherein the restorative crowns are placed on teeth and/or implants. Traditionally, such restorations have been performed by forming a model by providing an impression of the relevant areas of a patient's mouth, developing a stone model from the impression, and fabricating a customized prosthetic device on the stone model. This process is cumbersome and requires excessive intrusion into the patient's mouth. However, the stone model usually provides enough accuracy to produce clinically accurate prosthetics.

Recently, intraoral scanning (IOS) has emerged as a preferred dental impression technique for conventional (tooth-borne) and implant dentistry. Intraoral scanning typically involves using a handheld scanner having optical sensors to capture a three-dimensional (3D) dataset of an area of interest. The resulting dataset may be used for constructing a model for preparing patient specific prosthetics. The intraoral scanning process offers a very efficient and cost-effective means by which to acquire and transmit anatomic data for purposes of forming a prosthetic. While the accuracy of intraoral scanning has been proven to be sufficient for single tooth restorations and short-span multiple tooth segments (local accuracy), it is often contraindicated (provides insufficient general accuracy) for scanning larger segments such as full or partial arch areas, notably if an edentulous area is present.

Accuracy is typically described as being composed of trueness (for example, how much a true dimension of the object deviates from its measured size) and precision (for example, how much individual measurements vary in trueness with respect to one another). Imaging inaccuracies introduced over extended regions of an oral arch potentially result from stitching errors, in which a plurality of stitched images, each of which may be both true and precise internally, are misaligned with respect to one another. This can produce an overall decrease in the accuracy of the reconstructed oral arch, since the errors can build in a "random walk" and/or systematically along the extent of the arch.

While intraoral scanning and stitching is robust in presence of well-defined natural and/or implanted landmarks, lack of those in homogenous areas which are large with respect to the field of view can easily lead to divergence of the model. Unfortunately such areas are common in dental intraoral surgery, considering material and overall system limitations.

One proposed solution has been to spray the connecting geometry area with coating in order to help establish scannable registration features within the connecting area. The arch and the connecting area are then scanned and a resultant dataset is produced. It is assumed that some elements of the connecting area, such as the tongue, contain geometry sufficiently distinguishable for providing robust data. Potentially, however, the spraying technique still results in inaccurate scans; for example, due to possible drift of registration as elements shift from the location captured during the scan. Even if the elements are stable and with sufficiently distinguishable geometry and/or colorimetry, some proportion of scans is potentially subject to greater error using different oral scanning technologies (Meer et al. Application of Intra-Oral Dental Scanners in the Digital Workflow of Implantology, PLoS One 2012; 7(8); e43312). Furthermore, scanning protocols specifically adjusted to increase accuracy potentially slow down scanning.

SUMMARY OF THE INVENTION

There is provided, in some embodiments, a system, device and/or method for improving the accuracy of full oral arch or partial oral arch scans with intraoral scanners by introducing a fiducial marker on the oral arch. The fiducial marker may be used as a reference point for a designated location within the oral cavity. The fiducial marker may be scanned by the intraoral scanner and used in an algorithm for correcting an accumulated scanning error, which may have otherwise been accrued during standard, unmarked, full or partial arch scanning.

There is provided, in accordance with some exemplary embodiments, a method of reconstructing oral geometry using optical intraoral scanning, comprising: optically scanning a plurality of oral regions; positioning each of a plurality of rigidly interconnected fiducial features adjacent to a corresponding portion of one of the oral regions; scanning the positioned fiducial features together with the corresponding adjacent oral portions; and determining the relative positions of the plurality of oral regions based on dimensions of the rigid interconnections of the fiducial features, and on the positions of the fiducial features relative to each corresponding adjacent oral portion.

According to some embodiments, the fiducial features are positioned outside of the oral arches, and the rigid interconnections cross within the oral arches.

According to some embodiments, the scanning of the fiducial features is from outside of the oral arch.

According to some embodiments, the scanning of the fiducial features is of the upper and lower arches simultaneously.

According to some embodiments, the scanning of the fiducial features is while the upper and lower arches are in static occlusion, and the geometry of the occlusion is undisturbed by the positioning of the fiducial element.

According to some embodiments, the fiducial features are positioned to obscure portions of the optically scanned plurality of oral regions.

According to some embodiments, the obscured oral portions comprise teeth.

According to some embodiments, the relative positions of the scanned oral regions are determined for both the obscured and unobscured portions of the scanned oral regions.

According to some embodiments, the rigid interconnections are dimensionally fixed.

According to some embodiments, a dimension of the rigid interconnections is an adjustable dimension.

According to some embodiments, the adjustable dimension is a length or an angle.

According to some embodiments, the adjustable dimension of the rigid interconnections is determined by a reading from a scale marking or an electronic encoder.

According to some embodiments, the adjustable dimension of the rigid interconnections is determined by a dimension in a scan of an adjustably-sized region of an oral insert comprising the rigidly interconnected fiducial features.

According to some embodiments, the rigid interconnections cross unscanned oral regions.

According to some embodiments, the fiducial features are rigidly interconnected to form an oral insert.

According to some embodiments, the dimensions of the rigid interconnections of the fiducial features locate portions of separate fiducial marks to an accuracy and precision within 50 μm.

According to some embodiments, the dimensions of the rigid interconnections of the fiducial features locate portions of separate fiducial marks to an accuracy and precision within 100 μm.

According to some embodiments, the plurality of oral regions comprises regions of an oral arch.

According to some embodiments, the relative positions of the plurality of oral regions are determined for at least two regions which are discontinuous in image data provided by the scanning of the plurality of oral regions.

According to some embodiments, the determining comprises constraining the shape of the geometrical reconstruction based on the positions of the fiducial features relative to corresponding adjacent oral portions.

According to some embodiments, constraining the shape of the geometrical reconstruction comprises correcting out-of-true positions of the geometrical reconstruction based on the positions of the fiducial features relative to corresponding adjacent oral portions.

According to some embodiments, positions in the geometrical reconstruction away from the adjacent oral portions are adjusted by interpolating corrective transformations between the adjacent oral portions on which the correcting of out-of-true positions is based.

According to some embodiments, the scanning comprises scanning of distinct scan field regions; the geometrical reconstruction comprises stitching together of images of the distinct scan field regions by determining stitch registration parameters; and positions in the geometrical reconstruction away from the adjacent oral portions are adjusted by redetermining the stitch registration parameters, constrained by the positions of the adjacent oral portions.

According to some embodiments, the fiducial features are carried on a plurality of plates, and the fiducial features on separate plates are separated from each other by at least two tooth positions.

According to some embodiments, the plurality of separate plates comprises at least three plates.

According to some embodiments, the plates are oriented to extend along tooth facial surfaces of an oral arch comprised in the scanned oral regions.

There is provided, in accordance with some exemplary embodiments, a fiducial element for constraint of oral arch geometry reconstructed from optical intraoral scan data, the fiducial element comprising an oral insert which removably fits into a mouth, and is shaped to extend over an occlusal surface of an oral arch to rigidly interconnect at least three fiducial features, the fiducial features being distributed over an extent of at least eight tooth positions.

According to some embodiments, the fiducial features are located at least two tooth positions apart from each other, along the oral arch.

According to some embodiments, at least one of the at least three fiducial features is positioned against surfaces on the buccal side of the oral arch.

According to some embodiments, at least one of the at least three fiducial features is positioned on a surface of the fiducial element which extends over an occlusal surface of the oral arch.

According to some embodiments, the oral insert is shaped as an insert with at least one arm and at least one of the fiducial features is positioned near an end of the arm.

According to some embodiments, at least one of a length of the arm and an angle of the arm is adjustable.

According to some embodiments, an adjustment of the arm is encoded by at least one of an electronic encoder and a marked scale.

According to some embodiments, the oral insert comprises at least one plate carrying at least one of the fiducial features.

According to some embodiments, the at least one plate is oriented to extend along a facial surface defined by a tooth position of the oral arch.

According to some embodiments, the insert is shaped to be held by clamping between jaws of the mouth; and, when held between the jaws, at least one plate extends over a portion of both maxillary and mandibular oral arches of the jaws.

According to some embodiments, the at least one plate is at least 5 mm wide along the extent of the oral arch.

According to some embodiments, the at least three fiducial features are held on at least three corresponding plates, and the plates are separated from each other by at least two tooth positions.

According to some embodiments, the oral insert is formed with an outer layer of flexible material at a region where the rigid interconnections cross an oral arch when the oral insert is in the mouth, the layer of flexible material being configured to elastically deform when clamped between jaws of the mouth to fix the oral insert in position.

According to some embodiments, the oral insert comprises at least one LED.

According to some embodiments, the oral insert comprises a scannable code, and the code indicates a geometry of the oral insert specifying one or more distances between the plurality of fiducial features.

According to some embodiments, the oral insert comprises an arcuate surface shaped to face an occlusal surface when held between occlusal surfaces of a maxilla and a mandible; and wherein the fiducial features comprise at least one contour line extending along the arcuate surface and at least partially lingual or buccal to the oral arch.

According to some embodiments, the oral insert also comprises a surface facing buccally from the oral arch; and wherein the surface facing buccally comprises at least one of the fiducial features.

According to some embodiments, the fiducial features are rigidly interconnected to relative distances determined within an accuracy of 30 μm.

There is provided, in accordance with some exemplary embodiments, a fiducial element for constraint of oral arch geometry reconstructed from optical intraoral scan data, the fiducial element comprising an oral insert which removably fits into a mouth, and is shaped to fit within an oral arch and to rigidly interconnect at least three fiducial features, wherein the fiducial features are located at least two tooth positions apart from each other, along lingual surfaces of the oral arch.

There is provided, in accordance with some exemplary embodiments, a fiducial element for constraint of oral arch geometry reconstructed from optical intraoral scan data, the fiducial element comprising: an oral insert which removably fits into a mouth to position a plurality of fiducial features therein; and a light collection aperture of an imaging camera, oriented to collect imaging light from the fiducial features; wherein the fiducial features and the light collection aperture are rigidly interconnected to determined positions with respect to one another.

According to some embodiments, imaging by the imaging camera is activated upon contact being sensed by least two of the plurality of contact sensors.

There is provided, in accordance with some exemplary embodiments, a system for reconstructing oral geometry using optical intraoral scanning, comprising a geometry constraint module configured to: receive optical scan data from a plurality of oral regions; receive fiducial scan data comprising scans of rigidly interconnected fiducial features, each positioned adjacent to a portion of the plurality of oral regions; and determine the relative positions of the plurality of oral regions based on dimensions of the rigid interconnections of the fiducial features, and on the positions of the fiducial features relative to each corresponding adjacent oral portion.

According to some embodiments, at least one of the dimensions of the rigid interconnections is provided to the constraint module by a fiducial interface in communication with an encoder of the fiducial element to determine the at least one of the dimensions of the rigid interconnections.

According to some embodiments, the system comprises a fiducial element configured as an oral insert which removably fits into a mouth to position a plurality of fiducial features therein.

According to some embodiments, the scanning comprises scanning of distinct scan field regions, and wherein a scanned and field region with and without a fiducial feature in place overlap by at least 70%.

According to some embodiments, the oral insert is formed with an outer layer of flexible material at a region where the rigid interconnections cross an oral arch when the oral insert is in the mouth.

According to some embodiments, the layer of flexible material elastically deforms when clamped between jaws of the mouth to fix the oral insert in position.

According to some embodiments, the insert is shaped to be held between jaws of the mouth; and, when held between the jaws, at least one plate extends over a portion of both maxillary and mandibular oral arches of the jaws.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 14 is a simplified schematic illustration of a fiducial element within an oral cavity at an open state, according to some embodiments of the present disclosure;

FIG. 15 is a simplified schematic illustration of a fiducial element within an oral cavity at an open state, according to some embodiments of the present disclosure;

DESCRIPTION OF SPECIFIC EMBODIMENTS OF THE INVENTION

Figure 2:
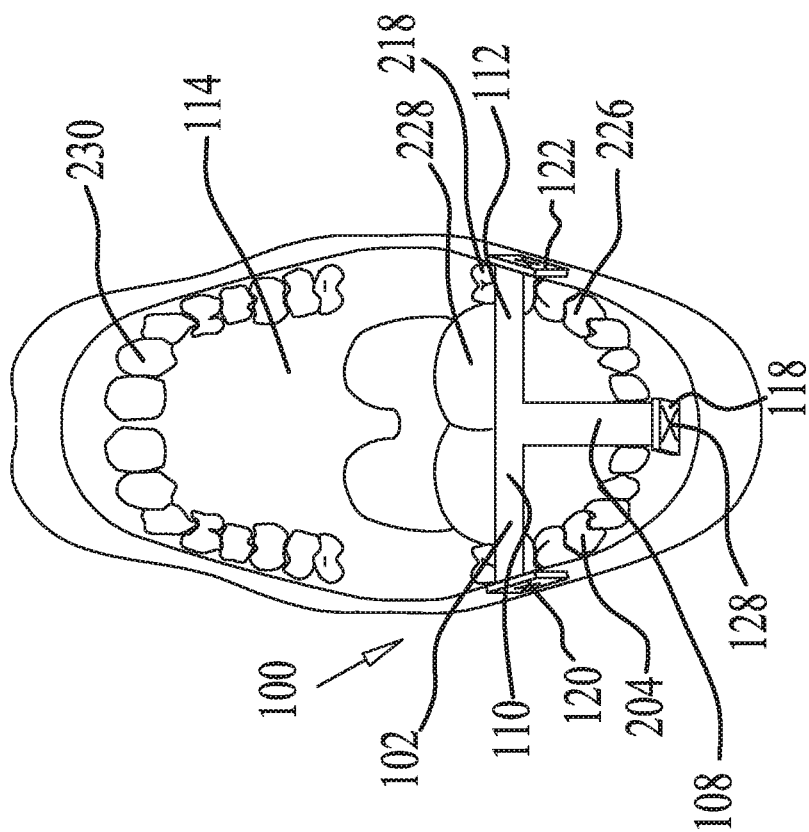
FIG. 2 is a simplified schematic illustration of the fiducial element of FIG. 1 within an oral cavity at an open state, according to some embodiments of the present disclosure.

This disclosure relates to dental scanning techniques, and specifically to systems, devices and methods for accurate intraoral scanning of a full or partial arch.

A broad aspect of some embodiments of the current invention relates to the constraining of 3-D reconstructions of oral scans to reduce geometrical inaccuracy.

Intraoral scanning robustly supports production of 3-D reconstructions of oral geometry when scanning well defined landmarks (i.e., teeth vs. tissue) in a relatively small area (e.g. a few teeth, for example 1-4 teeth). Such reconstructions are used, for example, in the preparation of restorative dental work to achieve close spatial tolerances. However, scans of larger areas, and in particular large homogenous areas, such as may be scanned in preparation for full arch restoration, are potentially problematic.

Some scan reconstruction errors occur where non-homogeneous scan segments are lacking (e.g., due to missing teeth). Teeth potentially provide robust landmarks in a scan of an arch, but soft-tissue surfaces between segments of the arch, such as the mouth surfaces, the gingiva, and the tongue, are relatively homogenous surfaces, potentially providing fewer and/or more ambiguous anchor points. Consequentially, the accumulated error during the scan may be larger. Furthermore, small adjacent site-to-site registration errors, while having minimal impact on a single tooth or short-span multiple tooth segments, potentially accumulate to unacceptably large cumulative error, for example throughout the full arch.

In some instances, as a result of errors such as these, the accuracy obtained for a full arch impressions taken by 3-D reconstructions based on intraoral scans (for example) is potentially in the range, for example, of about 30-50 µm, 30-100 µm, 30-500 µm, 30-600 µm, 30-800 µm, or in another range having the same, larger, smaller, and/or intermediate bounds. Required accuracy may be about 50 µm, in a non-limiting example. Required accuracy can depend on the circumstances to which the 3-D reconstruction will be applied. Natural teeth can move slightly (for example, in the range of about 50-100 µm) to adjust to impression inaccuracies in restorative dental work. However, existing artificial implants potentially allow less movement in at least one direction, for example due to bone compression. This can lead to a higher requirement for impression accuracy.

An aspect of some embodiments of the current invention relates to use of an exogenous fiducial element positioned in the mouth, and serving as a geometrical constraint on oral geometry.

In some embodiments, an exogenous fiducial element is used to supply geometrical constraints to decrease error in impressions produced from intraoral scans. For example, one or more separately known distances between portions of a fiducial element (including, for example, an arch-spanning distance) are related to positions in the intraoral scan data. Then the known distances of the fiducial element optionally serve as geometrical constraints on how the intraoral scan data are converted into a 3-D reconstruction of oral geometry. This allows scanned oral regions which might otherwise be spatially related only through a series of intervening scan registrations to be constrained in their relative position by a smaller number of relatively simple and/or less error-prone measurements.

Optionally, the fiducial element is used with data from current intraoral scanners to create 3-D reconstructions of an arch impression. Reconstruction errors are reduced, for example, in full-arch scans, or scans spanning a large segment of an oral arch (for example, at least 40%, 50%, 60%, or another larger, smaller or intermediate fraction of an oral arch). Optionally, the exogenous fiducial element is used to calibrate an intraoral scan dataset with known anchors to constrain reconstruction from the scanned dataset, potentially reducing reconstruction inaccuracies. In some embodiments, real-time constraint of a scanned dataset, based on fiducial element geometry, is performed as part of the process of acquisition of scan data points. Potentially, use of the fiducial element is fast and easy without adding complicated requirements to the work of the dentist or technician.

In some embodiments, there is a provided a fiducial element which reaches to a plurality of oral arch regions to present surface details which are in well-defined locations relative to one another. These spatial relationships optionally comprise a spatial frame of reference which serves to constrain reconstruction of the geometry of one or both of the oral arches, in whole or in part. In some embodiments, an oral arch geometry is reconstructed from a collection of digitally registered, partially-overlapping scans made along all or part of the oral arch. Optionally, the chain over overlapping scans is such that open-loop errors accumulate in moving between the left and right arms of the oral arch. For example, a small angular inaccuracy in an initial scan registration (e.g., an image stitch) on one side of the arch potentially propagates to become a large out-of-true positional inaccuracy on the other side. Additionally or alternatively, cumulative angular or translational errors at different stitch locations potentially result in a "random walk" error which is larger than any individual registration error.

In some embodiments, distances defined between fiducial marks by the interconnecting fiducial element are fixed. In some embodiments, the distances are adjustable, but rigidly held once adjusted. The frame of reference thus established is potentially used as a direct Cartesian geometry (features at points in a coordinate space), and/or as a set of features having known spatial relationships to one another (e.g., relative distances and angles, and/or offsets therefrom). In some embodiments, the distances are moreover determined with an accuracy of 100 µm or less, 75 µm or less, 50 µm or less, 30 µm or less, 20 µm or less, 10 µm or less, or another greater, smaller/and or intermediate accuracy. With one such distance defined, the constraint defines an arc of relative locations. With at least two such distances defined (for example, among at least three fiducial feature locations), the constraints are tighter. In some embodiments, at least 2, 3, 4, 5, 6, or more fiducial features are available at spacings of (for example) at least one tooth position, two tooth positions, or more. In some embodiments, at least three fiducial features are provided at positions of: the front four teeth, and on the left and right arms of the oral arch beyond the front four teeth.

In some embodiments, use of the fiducial element comprises scan imaging of fiducial marks, the mutual positions of which are determined by methods other than reconstruction of a connecting spatial model. For example, the distances are known according to a preset (optionally fixed) geometry of the overall fiducial element. Optionally or alternatively, the distances are determined by reference to a scale and/or readout associated with a distance and/or angle of the fiducial element.

Optionally or alternatively, the distances are determined by scanning of a portion of the insert from which an overall dimension can be inferred. For example, a length of an adjustable segment over a strut is scanned and analyzed for length; combined with other known dimensions of the device (even parts which are not imaged), relevant dimensions between fiducial marks are determined. Optionally, an adjustable angle is determined by scanning a join region, and the result used to calculate an overall separation between two fiducial marks.

In some embodiments, fiducial marks can assume any surface shape or contrast difference detectable by a scanner. Sharp boundaries with components extending in two or more at least partially orthogonal directions are of particular use as fiducial marks (since they are potentially easier to register), and may also provide an advantage by allowing precise definition of distances. Shape marks have the potential advantage of being detectable in 3-D scan data. Examples of features particularly suitable for shape marks include surface edges and corners, lines (etched or embossed, for example), and/or line crossings. Contrast differences (for example, surface reflectance differences) are potentially useful for embodiments of 3-D scanners which also capture features of object surfaces.

In some embodiments, a method of scanning comprises a first scan (also called a standard scan herein) of mouth regions which are to be reconstructed (optionally without any fiducial marks present), and then a second scan (also called a fiducial scan herein) with the fiducial marks present. In some embodiments, the fiducial marks are placed in a portion of the same scan fields as were obtained in the first scan; for example, so as to occlude a portion of the mouth geometry which was scanned in the first scan. Features visible in both the first and second scans are registered to one another. Optionally, the scan data are taken from each of the two scans for two closely similar scan fields (70% overlap, 80% overlap, 90% overlap, or another greater, lesser, or intermediate degree over overlap). Potentially, this reduces scan-to-scan registration error.

The positions of fiducial features (such as marks) in the fiducial scan optionally serve as constraints on the positions of nearby oral arch features. Transferring these constraints to the corresponding features of the standard scan, in some embodiments, provides a basis for correction of inaccurate (for example, out-of-true) reconstruction features.

Fiducial features are optionally present buccally, lingually, and/or over the crown. The fiducial features optionally are viewed from a generally buccal, lingual, and/or occlusal direction.

An aspect of some embodiments of the current invention relates to an oral insert comprising fiducial targets held rigidly interconnected with each other.

In some embodiments, the oral insert comprises plates, one or more portions of which serve as fiducial targets. Optionally, the plates are positioned to be held within the mouth against and/or overlying tooth facial surfaces (i.e., buccal and/or labial surfaces) of the oral arch, and/or in positions where the facial surfaces of teeth would be located in a complete oral arch, as defined, for example, by anatomical structures indicating a tooth position. Optionally, the fiducial targets are positioned to be held within the mouth against occlusal surfaces.

In some embodiments, the oral insert comprises an imaging device (a camera and/or scanner, for example), which is also held in a rigid spatial relationship with the fiducial targets. Optionally, the imaging device is positioned to allow imaging of the fiducial targets. Optionally, imaging by the imaging device is triggered by sensing of contact (for example, at two, three, or more contact-sensing positions) between the oral insert and surfaces of the mouth.

In some embodiments, fiducial targets are positioned such that a substantial portion of the oral arch (e.g., a portion comprising teeth) is visible adjacent (for example, immediately adjacent) to the fiducial targets. A substantial portion comprises, for example, a portion which is large enough that a unique position in 3-D space can be determined for a 3-D scan of it, relative to a scan comprising up to most or all of the teeth of the oral arch. Optionally, a substantial portion comprises at least a whole aspect of a tooth, and/or at least an aspect of gap region between teeth comprising a portion of a tooth on at least one side.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1:
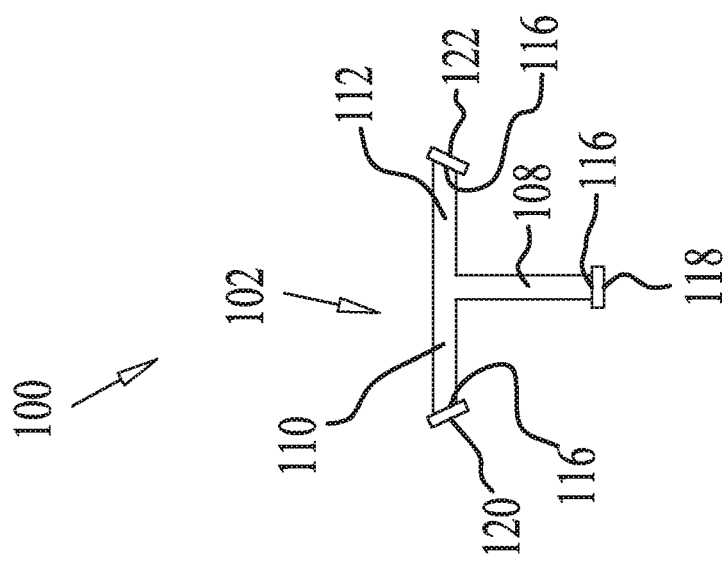
FIG. 1 is a simplified schematic illustration of a fiducial element according to some embodiments of the present disclosure.
Figure 3:
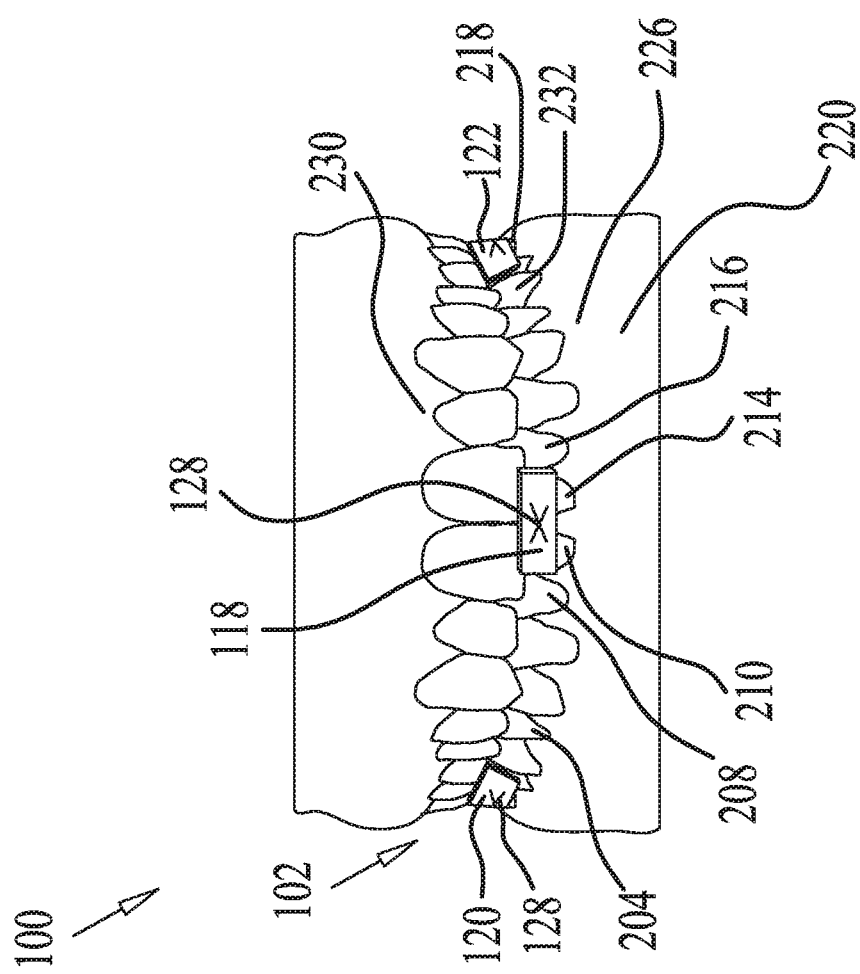
FIG. 3 is a simplified schematic illustration of the fiducial element of FIG. 1 within an oral cavity at a closed state, according to some embodiments of the present disclosure.

FIGS. 1-3 are each a simplified schematic illustration of a fiducial element 100 according to some embodiments of the present disclosure. As seen in FIG. 1, the fiducial element 100 may be configured as an oral insert 102. The oral insert 102 may be formed in any suitable manner, such as a T-shaped insert including a central longitudinal bar 108 and a branching (for example, generally perpendicular) first arm 110 and second arm 112.

Optionally, any location on the oral insert 102 is used as a fiducial marker to mark a reference point within an oral cavity 114 (FIG. 2). In some embodiments, the location may be any one of edges 116 of the bar 108 and arms 110 and 112. It is a potential advantage for the fiducial marker to comprise a geometrical landmark, such as a corner, edge, indentation, and/or engraving, as these are directly revealed by 3-D scanning. Geometrical landmarks preferably include a shape having at least one sharp change of surface plane. Surface reflection information (e.g., color) is alternatively or additionally used to distinguish fiducial mark locations.

In some embodiments, at the edge 116 of at least one of the bar 108 and arms 110 and 112 may be attached respective plates 118, 120 and 122.

The plates 118, 120 and 122 may be attached to respective bar 108 and arms 110 and 112 in any suitable manner to fit within the oral cavity 114. For example, the plates may be attached substantially parallel to the edge 116, such as seen at plate 118, which is substantially parallel to edge 116 of bar 108. Plates 120 and 122 are shown to be attached at an incline in respect to edges 116 of arms 110 and 112. Any one of the plates 118, 120 or 122 may be used as a fiducial marker to mark a reference point within the oral cavity 114.

In some embodiments, on any one of plates 118, 120 or 122 may be etched, or in any manner marked, a fiducial marker or character 128 formed in any suitable configuration, such as an "X" character shown in FIGS. 2 and 3. In particular, markings comprising crossings or corners defined by straight lines (e.g., a grid, "X", "+", "<", "A", or another such shape) provide a potential advantage for localization of the crossing/corner, since multiple measurement points potentially constrain each other to indicate a focal region in space. A potential advantage of etching is an effect on the scanned 3-D shape of the plate. Optionally, oral scanner reconstructions combine 3-D shape with surface reflectance properties (such as color, where color imaging is used), allowing use of flat-marked fiducial targets as well or alternatively. Optionally, characters 128 may be used as a fiducial marker to mark a reference point within the oral cavity 114.

Optionally, the oral insert 102 including the plates 118, 120 and 122 is be formed of any suitable material, such as stainless steel, or any other dentally compatible material. In some embodiments, the oral insert 102 including the plates 118, 120 and 122 may be formed of molded plastic.

Optionally, the oral insert 102 is used repeatedly (for example, after resterilization); additionally or alternatively, it is disposable.

The plates 118, 120 and 122 may be formed in any suitable shape or size. For example, the plates 118, 120 and 122 may be formed as a square with a side length of approximately 5 mm long and a thickness of approximately 1 mm. In another example, the side may have a length in the range of approximately 1-10 mm and a thickness in the range of approximately 0.2-5 mm.

In other embodiments, the plate may be formed in a circular, ellipse or triangular shape, for example.

In some embodiments, fiducial targets (for example, plates) extend along the extent of the oral arch to a distance about the width of a single tooth, but can be larger or smaller. Vertical extent is optionally the same, but optionally is constrained to extend only partially vertically along the tooth. It is, for example, a potential advantage for registration to be able to scan the basal region of a tooth which the fiducial mark partially overlies.

Optionally, fiducial targets are thick enough to resist distortion during handling and/or upon placement. For example, a press- or clamp-fitted plate embodiment is optionally at least 1 mm thick to avoid distortion. Nevertheless, it is a potential advantage for the plate to be thin, for example in order to bring the scanned surface of the plate closer to the arch geometry which it is used to help characterize.

While a flat geometry such as shown in FIG. 1 indicates one preferred embodiment of a plate 118, 120, 122, herein a "plate" is optionally substituted by any scannable fiducial target which is positioned over and/or nearby native features along the oral arch (particularly against an inside or outside surface of the oral arch), and comprises a fiducial feature (e.g., a mark or geometrical feature) having a determined spatial relationship with a fiducial feature of another such fiducial target. A plate-like geometry, however, has potential advantages, for example, in that:

main visible surfaces extend substantially along planes, so that 3-D scanned positions scattered across each surface are optionally useful as strong constraints on each other's positions; and well defined edges of main surfaces provide good features for registration algorithms.

In some embodiments, a polygonal plate (such as a rectangular plate) is used, providing, in addition to the above, straight edges (point locations along which potentially also serve to provide mutual constraints), and/or well-defined corners (optionally used as registration features).

Moreover, in some embodiments (as described, for example, in relation to FIGS. 8-10 and 15), plates are positionable to tightly abut one or more surfaces of the oral arch geometry (such as tooth surfaces). Flat plate surfaces potentially constrain the location of contact, which potentially assists in constraining reconstruction of the oral arch geometry.

Despite these potential advantages, it should be understood that, in some embodiments, a non-plate geometry (such as a sphere, ellipsoid, comb, rod, mesh, or other shape) is used as the fiducial target. A spherical or ellipsoidal fiducial target potentially also has a self-constraining surface (defined radius) geometry, and is predictable in contact points in virtue of its regular surface shape; moreover it is a physically robust shape which potentially resists deformation that could interfere with measurement accuracy. A comb or mesh potentially provides a large number of edges which constrain registration, and/or to which native oral arch features can be more closely related. A rod shape is easily made thin (for example, about 1 mm in diameter) to create a fiducial mark which minimally interrupts a scanner's view of surrounding native oral arch features.

The bar 108 and arms 110 and 112 may be formed of any suitable shape or size. For example, the thickness of the bar 108 and arms 110 and 112 may be in the range of approximately 0.2-5 mm. In some embodiments, plates 118, 120, 122 are held with respect to one another by a mouth insert geometry with another shape, for example as described in relation to FIGS. 7A-11. A potential advantage of a bar/arm shaped mounting is that it is easily placed in a wide variety of mouth shapes and/or sizes.

In some embodiments, fiducial targets such as plates 118, 120, 122 are held by bar 108 and arms 110, 112 (or by another mouth insert geometry) at rigidly determined distances from one another. In some embodiments, the rigidly determined distances are predetermined and fixed (adjustable but rigidly determined distances are described, for example, in relation to FIGS. 8-10). Optionally, the distances are determined with respect to well-localized fiducial features such as edges, corners, lines, and/or crossings. Optionally, the distances are determined with respect to abstract features (such as a center position on a plate), but it can be understood that distances are optionally offsetable to also determine distances between well-localized fiducial features.

Optionally, distances are determined within 3-D coordinates (for example, a spatial distance between the center points of two corners or crossings on different fiducial scanning targets). Optionally, distances are determined within a plane—for example, the distance between two vertical (and substantially parallel) edges on two separated fiducial targets. It is easily understood that knowing the total geometry of the fiducial element 100 (for example, as manufactured) allows determining the distance between any two sufficiently well-localized features of the element 100. However, it is a potential advantage to focus analysis on dimensions which are most likely to be stable, and/or which are easily selected in the design of the fiducial element 100, such as distances extending along bar 108 or arms 110, 112. Furthermore, some distances need to be stable and/or readily determined by a reading across large (and optionally unscanned) extents of the mouth, while short-range distances (e.g., distances falling on a single fiducial target and/or within the scope of a single scan pass) are potentially determined by offsetting from one or more determined longer distances, the offsetting being based on scanning data.

Based on its determined dimensions, the fiducial element 100 may be used as a reference to increase accuracy of a dataset of a full or partial scan of the oral cavity 114. Briefly, in some embodiments, distinct mouth regions (in particular, oral arch regions) near to different portions of the fiducial element 100 are potentially subject to errors in scan-determined positioning. Knowing distances between different portions of the fiducial element 100 from one or more non-scan dependent sources allows the application of geometrical constraints to the scan data that potentially reduce those errors.

Scanning is optionally performed by any suitable scanning method 200 and data processing method 250, for example as described in the respective flowcharts of FIGS. 4A-4B and 5A-5B. It is appreciated that the method 200 or 250 may be realized in any suitable manner.

Figure 4A:
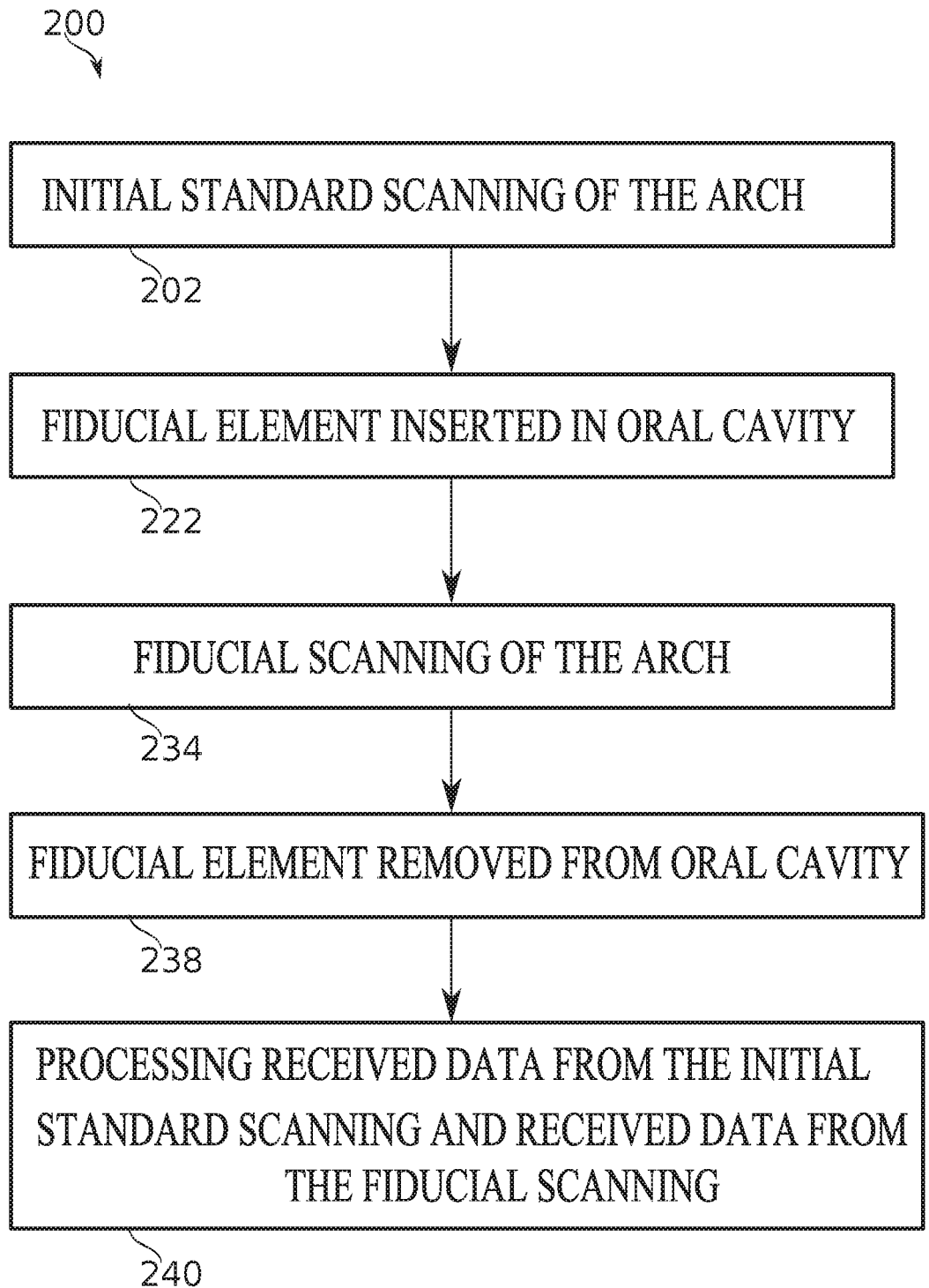
FIG. 4A is a simplified flowchart of a scanning and data processing method using the fiducial element, according to some embodiments of the present disclosure.
Figure 4B:
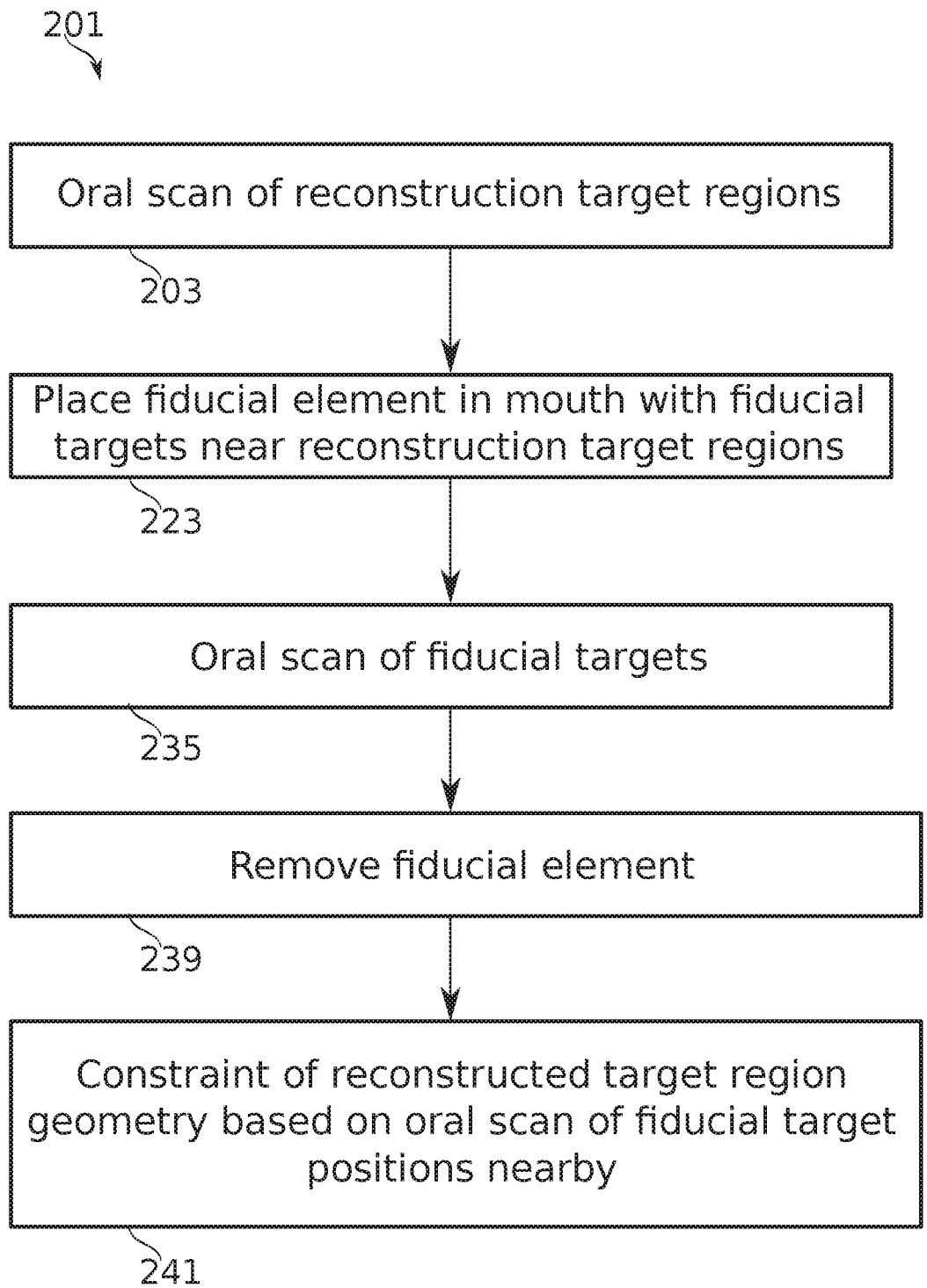
FIG. 4B is a simplified flowchart of an alternative scanning and data processing method using the fiducial element, according to some embodiments of the present disclosure.

Reference is now made to FIG. 4B, which schematically illustrates a method 201 of oral scanning for fiducial element-guided correction of scan error, according to some embodiments of the disclosure.

At block 203, in some embodiments, 3-D oral scanning of mouth regions for which geometrical reconstruction (that is, computerized modeling of the 3-D geometry) is performed. The mouth regions optionally comprise complete or partial oral arches. Optionally, mouth regions are scanned disjointly (that is, without initially ensuring that the scanned regions together form a contiguous scan region). Optionally, the resulting mouth region data is of disjoint regions (that is, regions which actually do not together form a contiguous scan region).

At block 223, in some embodiments, a fiducial element is placed in the mouth with fiducial targets (held in rigid relationship to one another by the fiducial element) positioned near reconstruction target regions. In some embodiments, the fiducial targets are held near reconstruction target regions such that some portions of the regions are obscured (by the fiducial targets themselves, for example, and/or by other structure of the fiducial element), and others, nearby fiducial targets, are visible (unobscured). In some embodiments, fiducial targets held overlying target regions are optionally transparent at least in part; however, the underlying region is still "obscured", at least in the sense of its 3-D surface structure being masked by the overlying fiducial element. In some embodiments, a fiducial target is held overlying and/or obscuring a portion of the basal-to-crown extent of a portion of an oral arch. In some embodiments, a fiducial target is oriented in the occlusal plane, and it (and/or a supporting portion of the fiducial element) overlies and/or obscures a portion of the occlusal surface of an oral arch.

Additionally or alternatively, the criteria governing placement emphasize adjacency. For example, a fiducial target is held adjacent to an oral region to be reconstructed in 3-D; sufficiently close that accuracy in determining their relative locations is controlled by the accuracy of the scanning device, rather than data registration occurring during reconstruction. For example, the two features (fiducial and oral) occupy a common scan frame and/or scan line. Optionally, the adjacent regions include regions immediately adjacent to the fiducial targets. For example, the fiducial target optionally contacts an adjacent region, and/or is contiguous with it in the 3-D scan data.

In some embodiments, the fiducial element is placed with sufficient stability that two or more sequential scans from different positions can be made without undue risk of movement between the scans. In some embodiments, the elements are placed and imaged so that a single scan establishes the relationship of two or more well-separated fiducial targets and the oral geometry.

At block 235, in some embodiments, an oral scan including fiducial targets and adjacent regions of the oral arch is performed.

Optionally, the fiducial targets occupy at least two distinct regions separated by at least one, two, three, four, or more tooth positions (teeth or tooth sockets). Additionally or alternatively, the fiducial targets are distributed over at least six, seven, eight, nine, or ten tooth positions, or over a larger or smaller number of tooth positions. Optionally, the fiducial targets comprise two fiducial targets on opposite sides of the oral arch, for example, spaced at least four, five or more tooth positions away from the center or front of the oral arch. Optionally, at least a third fiducial target is positioned within one or two tooth positions of the center or front of the oral arch. Preferably, the fiducial target scans include enough of each adjacent reconstruction target region to allow matching to another image of the same region, through which matching the geometrical constraints of the fiducial element can be transferred to the reconstruction of the oral arch itself. In some embodiments, the fiducial target scans include enough of each fiducial target to allow determination of the distance between fiducial targets based on known geometric constraints established by the fiducial element overall.

At block 239, in some embodiments, the fiducial element is removed.

Figure 5A:
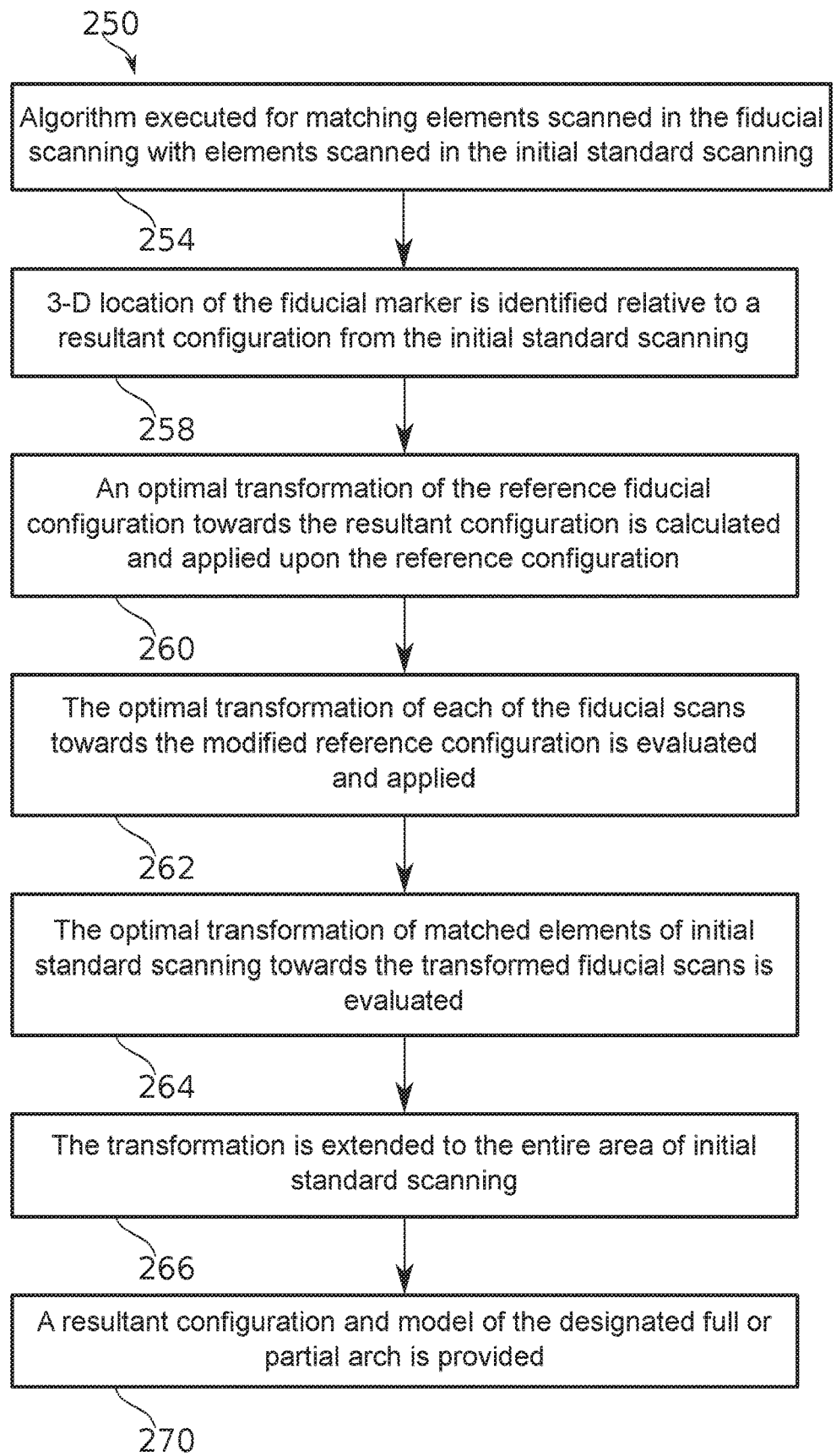
FIG. 5A is a simplified flowchart of a data processing method using the fiducial element, according to some embodiments of the present disclosure.
Figure 5B:
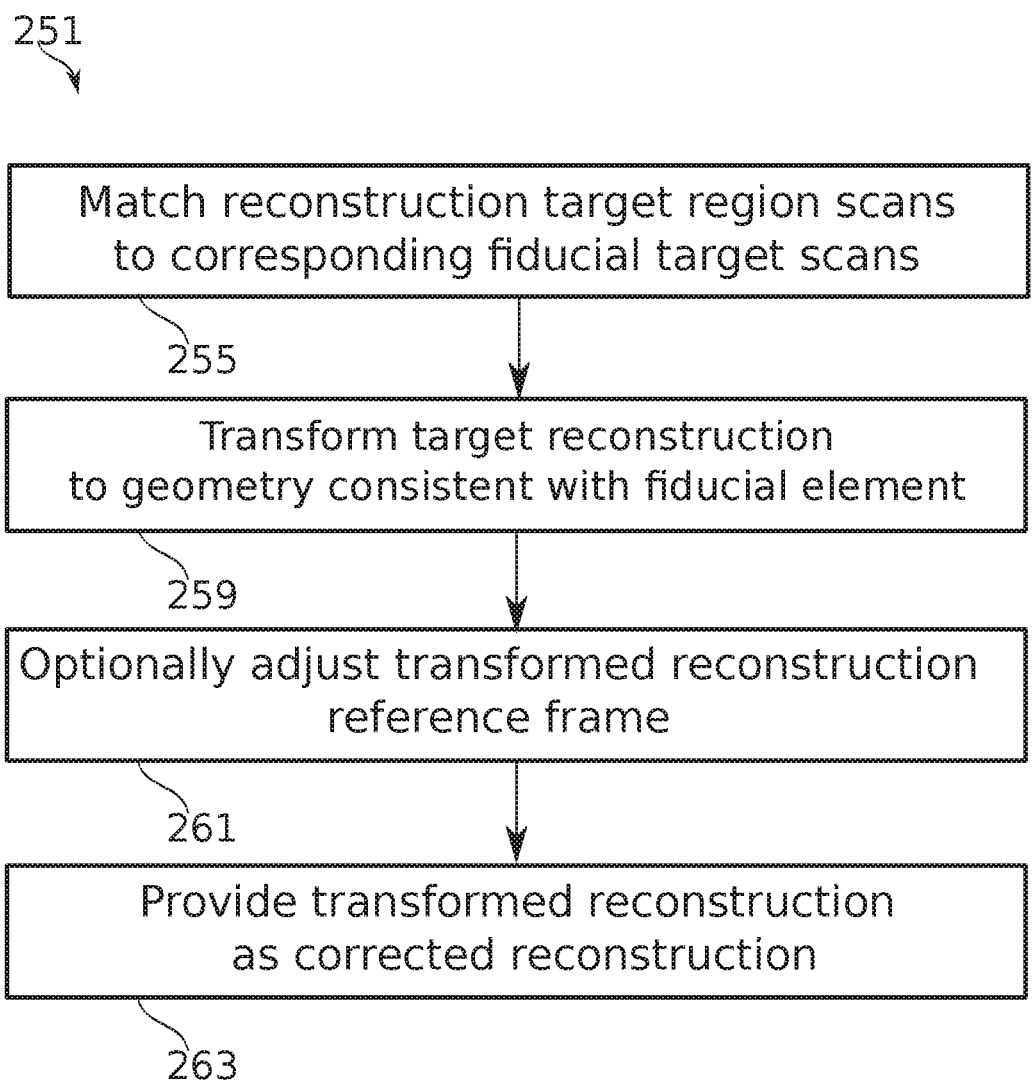
FIG. 5B is a simplified flowchart of an alternative data processing method using the fiducial element, according to some embodiments of the present disclosure.

At block 241, in some embodiments, processing occurs (for example, according to one of the methods described in relation to FIGS. 5A-5B) such that a computerized 3-D reconstruction of the target region geometry is constrained (optionally, corrected) according to the scan data acquired by the fiducial target scans and the known and/or separately measured geometry of the fiducial element which rigidly interconnects them.

Reference is now made to FIG. 4A, which is a simplified flowchart of another scanning and data processing method using the fiducial element, according to some embodiments of the present disclosure;

As seen in FIG. 4A: at block 202, in some embodiments, an initial standard scan of the designated full or partial arch 204 (FIGS. 2 and 3) is performed by intraoral scanning methods. Typically, the scanning is performed by using a handheld scanner including optical sensors for capturing a 3-D dataset of the designated full or partial arch 204. In the intraoral scanning method, absent a reference point, conglomerate errors throughout the partial or full arch 204 may accrue. For example, as shown in FIG. 3, during standard intraoral scanning, at first the two left sided lower incisors 208 and 210 are scanned from lower incisor 208 to lower incisor 210. The scanning continues to adjacent two right sided incisors 214 and 216 and then to the other teeth, such as tooth 218. Yet due to the accumulated error, which accumulated during scanning, when the local single view 3-D models are stitched together, the location of, for example tooth 216 relative to tooth 218 is skewed and inaccurate.

To rectify this error the fiducial element 100 may be inserted at any suitable location within the oral cavity 114, as seen at block 222. In FIG. 2 the fiducial element 100 is shown placed upon the mandible 226 resting on the tongue 228. Optionally, the mandible 226 is tightly fixed to the maxilla 230 to prevent movement of the fiducial element 100, as seen in FIG. 3. The plates 118, 120 and 122 are placed at an external surface 232 (FIG. 3) of the teeth at the buccal side.

Once the fiducial element 100 is fixedly placed within the oral cavity 114, fiducial scanning of the arch 204 is performed, as seen in block 234. The fiducial scanning may be performed in any suitable manner, such as by the same intraoral scanning method used for the standard scanning of block 202. For example, 3-D scanning of each of the fiducial markers, such as plates 118, 120 and 122, may be performed such that each plate is scanned along with fiducial marker 128 and a surrounding area of uncovered teeth. The fiducial scanning may be of each of the plates and a surrounding area without requiring scanning of the complete designated arch. Optionally, the scan performed at block 202 is partial (that is, comprises gaps in the extent of the scanned data), so long as scanned fragments can be related to one another though the geometry of the fiducial element 100.

In the example of FIGS. 2 and 3, three fiducial scans are optionally performed: one of plate 118 and the surrounding area, one of plate 120 and the surrounding area and one of plate 122 and the surrounding area. Potentially, this fiducial scanning is very short, since it may require only a single image taken by the scanner (including a three scans). Scan time itself for each fiducial is optionally about 0.1 seconds. Optionally, the scanning is up to a few minutes long.

A potential advantage of having the fiducial targets appear on the buccal side of the oral arches, with connecting elements passing over the oral arches, is that the fiducial element 100 is optionally fixed in place simply by clamping by the jaw. Further potential advantages comprise the relative ease, rapidity, and/or comfort of scanning from the buccal side (particularly from the front). Another potential advantage, in some embodiments is that simultaneous (and potentially faster) acquisition of correction data for both the maxilla 230 and mandible 226 is possible, since the fiducial targets are positioned between them.

In some embodiments, the fiducial element is constructed so that buccal fiducial targets are held in place, and fixed relative to one another, without disturbing the occlusion (for example, without disturbing the normal static occlusion of the patient). For purposes of measurement, an undisturbed occlusion is entirely undisturbed (no displacement in relative positions of the oral arches), or comprises displacement of no more than 10 μm, 15 μm, 30 μm, or another larger, smaller, or intermediate displacement. For example, the fiducial element comprises an arcuate (or otherwise shaped) body fitting around the outside of an oral arch, which is sufficiently rigid to stabilize the relative position of the fiducial targets. The arcuate body itself is optionally secured, for example, by members (optionally thin members such as wires) which pass lingually through natural occlusion gaps, and/or are sufficiently delicate and/or thin that they do not disturb the occlusion (e.g., are bitten through or displaced where teeth meet), or disturb the occlusion within acceptable tolerances. In some embodiments, for example, a 25 μm-thick (or other larger or smaller thickness), polymer membrane is attached to the rigid body which passes over the occlusal surface of the teeth. In some embodiments, thin fibers pass between parts of the rigid body, strung tightly enough to hold it in place, but flexible enough to be pushed away from regions of close occlusion when the jaws are closed. Additionally or alternatively, the rigid portion of the arcuate body is provided with a fitting element which is flexible for fitting engagement with the oral arch. The fitting by the fitting element comprises, for example, soft deformation of a material in which the rigid body is partially embedded, and/or elastic deformation to clamp the outside of a portion of the oral arch. A potential advantage of such embodiments is to allow simultaneous acquisition of occlusion scan data and fiducial mark scan data. This is a potential advantage for increasing the speed and/or ease of overall scan acquisition, while maintaining the use of an exogenous fiducial element for correction of scan inaccuracies.

In some embodiments, upon completion of the fiducial scanning of block 234, a small area, such as a portion of plate 118 and an adjoining area, may be rescanned to ensure the fiducial markers did not inadvertently move during the fiducial scanning.

As seen in block 238, the fiducial element 100 may be removed from the oral cavity 204.

Thereafter, as seen in block 240, received data from the initial standard scanning of block 202 may be processed with received data from the fiducial scanning of block 234 in any suitable manner.

Reference is now made to FIG. 5B, which schematically illustrates a method 251 of correcting target region scans according to corresponding fiducial target scans, according to some exemplary embodiments of the disclosure. Another exemplary processing method 250 is shown in the flowchart of FIG. 5A.

The method of FIG. 5B illustrates a method of correction 251 in overview. A more detailed embodiment, along with optional variations and/or alternatives, is described in relation to FIG. 5A.

At block 255, in some embodiments, scans of target regions used for intraoral geometry reconstruction are matched to corresponding fiducial target scans. The matching is, for example, on the basis of imaged similarities of intraoral features nearby to fiducial targets (in the fiducial target scans) to intraoral features seen in the target region scans used as the main basis of intraoral geometry reconstruction. Optionally, the matching also takes advantage of position constraints known otherwise, for example, from the order of scanning, and/or from identifying marks on the fiducial targets which indicate general position relative to the oral arch.

At block 259, in some embodiments, a target reconstruction is transformed to a new geometry which is consistent with the geometry of the fiducial element. In some embodiments, this comprises altering a completed target reconstruction to fit within constraints established by known geometry of the fiducial element (and its fiducial targets), in view of the matching results of block 255. In some embodiments, a target reconstruction is initially incomplete, and the fiducial element geometry is used to complete it. This provides a potential advantage when reconstruction target region scans of an oral arch optionally comprise disjoint regions around the arch (there could be edentulous regions between them, for example). It should be understood that the transformation to a new geometry is optionally direct, or through a series of intermediate transformations.

At block 261, in some embodiments, the transformed reconstruction is optionally adjusted to a suitable reference frame. Whether or not this adjustment is applied optionally depends on how the transformation of block 259 is achieved. For example, in some embodiments, block 259 is accomplished by warping the oral geometry reconstruction into a coordinate system established by the fiducial element and its fiducial targets. However, subsequent processing may be preferably in a coordinate system which is (or is minimally deviated from) the frame of reference used for the initial scan.

At block 263, in some embodiments, the transformed reconstruction is provided as a corrected reconstruction. Again, it is noted that the terms "transformed" and "corrected" do not necessarily require that "uncorrected" and "untransformed" reconstructions be created as intermediate steps. In some embodiments, a reconstruction is first created already corrected.

As seen in FIG. 5A, a processing unit may be used along with data connection to the intraoral scanner to perform the following:

As seen in block 254, an algorithm is executed for matching (that is, spatially registering) the teeth and/or other oral regions scanned in each fiducial scanning of block 234 with the teeth and/or other oral regions scanned in the initial standard scanning of block 202.

In block 258, at least one 3-D location of each of the fiducial markers, such as plates 118, 120 and 122, portions thereof, and/or the characters 128, is identified relative to a corresponding location in the resultant configuration from the initial standard scanning.

In some embodiments, scans comprise images or image-like units of relatively well-determined (precise) points, with the most significant errors being introduced at the stitching stage (two images aligned out-of-true). This error potentially occurs not only during stitching of the standard scan images, but also when the fiducial scan images are registered to corresponding standard scans. Optionally, scan data acquisition for the standard and fiducial scanning operations is performed such that images containing corresponding scan points are overlapping to a greater degree than chance (for example, overlapping, disregarding the loss of occluded areas, by at least 80%, 90%, or another greater, lesser, or intermediate value). This provides a potential advantage for reduction of errors by fiducial-to-standard scan registration, for example by ensuring that a high proportion of corresponding points are available, and/or by reducing potential ambiguity arising from registration to a composite region which was stitched out-of-true.

Optionally, fiducial markers (e.g., plates or regions thereof) are positioned by the mouth insert at places aligned to the boundaries expected from following a recommended scan protocol. For example, if the scan protocol specifies centering a tooth in a scan field, it is a potential advantage for the fiducial mark to be placed so that the registration features it bears are appropriately placed in a tooth-centering scan.

At block 260, in some embodiments, optimal transformation of the reference fiducial configuration towards the resultant configuration is calculated and applied upon the reference configuration. Calculation of the transformation is optionally based on the location correspondence previously identified between parts of the known geometry of the reference fiducial configuration, and the resultant configuration from the initial standard scanning. The optimal transformation is, for example, a best fit linear isomorphic transformation, optionally comprising rotation and/or translation.

At block 262, in some embodiments, an optimal transformation of each of the fiducial scans towards the modified reference configuration is evaluated and applied. Optionally, this comprises separately determining the transformation of each of the fiducial scans toward the reference configuration of block 260, according to the matching associations determined, for example, at block 258.

A potential advantage of the operations of block 260-262 is to bring the fiducial element coordinate system and the standard and fiducial scan coordinate systems into general alignment. Initial transformation toward the standard scan coordinate system allows generally conserving that scan's coordinate system, so that remaining adjustments remain relatively small. This can also be an advantage, for example, when presenting corrected and uncorrected reconstructions for comparison. If the coordinate system has been minimally disturbed, it is easier to visualize where the constrained reconstruction and the original reconstruction differ. This is a potential advantage for confirming that the process of correction has operated as expected (unusually large, or oddly-shaped corrections would more easily stand out, for example).

At block 264, in some embodiments, an optimal transformation of matched teeth and/or other oral regions of the initial standard scanning towards the transformed fiducial scans is evaluated. Optionally, this is performed preferably between fiducial and standard scan images with the highest available overlap. Optionally, the transformation is a linear transformation. Optionally, the linear transformation comprises translation and/or rotation. While a scaling constant is also optionally used, the types of mis-registration of greatest concern, in some embodiments, comprise translational and angular misalignments, so that scaling differences can be ignored.

At block 266, the transformation is extended to the entire area of initial standard scanning. In some embodiments, this comprises interpolation of transform coordinates found for the directly matched regions to other regions so that a substantially continuous gradient of error parameters is applied. Expressed in terms of trueness and precision: the mouth regions located by the fiducial marks are fixed in true, and, optionally, the imprecisions among the data points which cumulatively produce the initial trueness error are redistributed (e.g., the average trueness error is subtracted from regions along the oral arch) without necessarily identifying specific misalignments. This has the potential advantage of being a rapid and/or deterministic correction method.

Alternatively, for example, in embodiments where 3-D image stitching is used, registration constraints established by feature matches between the fiducial scan images and the standard scan images are treated as fixed boundary conditions. Optionally a new 3-D reconstruction is formed by adjusting image stitching parameters (for example, iteratively) until an internally consistent reconstruction is achieved. Expressed in terms of trueness and precision: the mouth regions located by the fiducial marks are fixed in true, and, optionally, new registrations found among stitched scan images which are both individually well-stitched (for example, there may have been an initial ambiguity in the scan data between a plurality of stitching positions), and collectively in true. A potential advantage of this approach is to allow correction of out-of-true stitching at the source; thus removing it, rather than redistributing the inaccuracy so that it cancels out globally.

In some embodiments, block 266 may be performed with the aid of conventional jaw structure model data. There may be a single general model, or a bank of models to be chosen from according to the specific scenario or features of the specific jaw. In some embodiments, local adaptation according to a partial model is performed. Reference to a conventional jaw structure model potentially allows local adjustments to locally out-of-true reconstruction regions. For example, angular deviations from a smooth (e.g. monotonically curving) jaw shape at stitching boundaries are optionally detected at a local level and reduced. Since the overall shape is held true at the fiducial marks, the risk of introducing corrections which unacceptably degrade the final fit is potentially reduced.

In some embodiments, a weighting is applied at step 266, taking into consideration classification of the structures and/or materials of the arch. For example, native teeth typically possess greater flexibility in position than implants. According to the weighting function, some portions of scanned data might be limited in transformation either locally or with respect to another position. Classification is based, for example, upon colorimetry, 3-D structure, and/or jaw modeling.

It should be understood that sequence of transformations described with respect to blocks 260-266 is optionally carried out by an alternative sequence of intermediate transformations, or in a concerted transformation. For example, in some embodiments, the standard scan data is optionally transformed initially into the fiducial reference configuration and adjusted there, then back-transformed to the coordinates of the original data, either by inversion of a previous transform, or by determination of a new optimal transformation. In some embodiments (for example, if the standard scan includes gaps), the reference fiducial configuration provides a coordinate system into which the standard scan data are integrated.

Following block 266, a resultant configuration and model of the designated full or partial arch 204 is provided, as seen in block 270.

Thus, is it is shown that there is provided a method for potentially improving full or partial arch scanning by introduction of the fiducial element 100. The fiducial element 100 is simple to use. Its maintenance may be simple and may be treated as other conventional dental tools, such as by sterilization in an autoclave. The fiducial scanning is as simple to perform as any conventional scanning method, and is of a relatively short duration.

Figure 6:
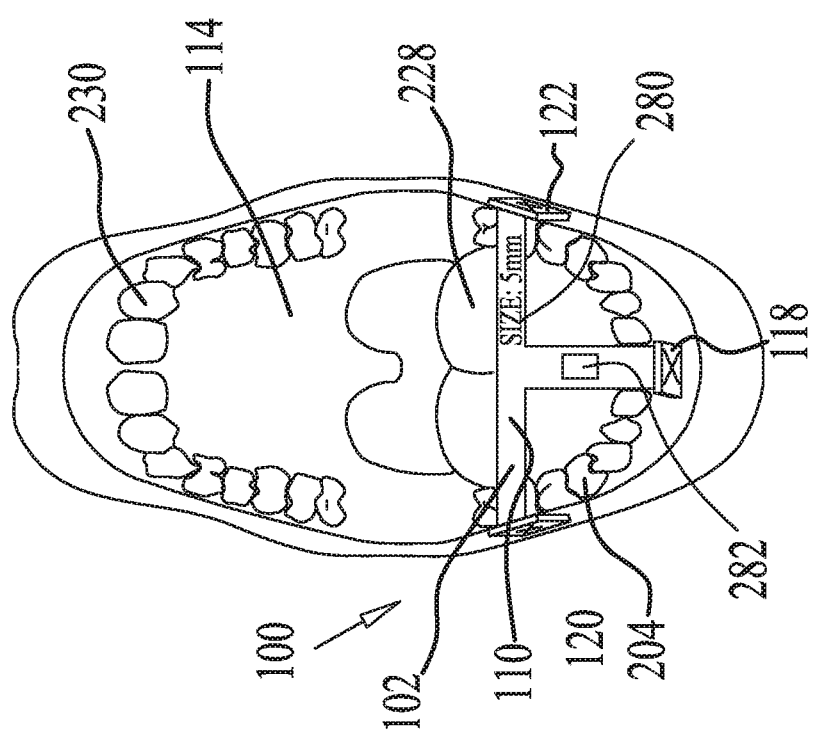
FIG. 6 is a simplified schematic illustration of a fiducial element within an oral cavity at an open state according to some embodiments of the present disclosure.

FIG. 6 is a simplified schematic illustration of the fiducial element 100 according to some embodiments of the present disclosure. In some embodiments, the oral insert 102 may be produced in a variety of sizes to fit different arch sizes, such as of adults and children. The size and any other relevant information may be inscribed on an inscription 280 on the oral insert 102 in any suitable manner, such by any inscription method that can be scanned by the intraoral scanner and may undergo sterilization. For example, the inscription 280 can be engraved or marked by laser technologies. By inscribing the oral insert information on the oral insert 102 itself, the insert information may be provided to the processing unit without requiring additional entry of the insert information.

In some embodiments, the insert information may include the size of the oral insert 102. For example, following manufacturing, the size of the oral insert 102 may be measured in any suitable manner, such as by an accurate dimension measuring device, e.g. a coordinate measuring machine (CMM).

The insert information can be provided to the processing unit in any suitable manner, such as by encoding the information as a two dimensional barcode or text or 3-D inscription and can be analyzed automatically by an optical character recognition (OCR) algorithm or any other suitable algorithm. The inscription 280 may be inscribed at any suitable location of the oral insert 102, such as on bar 108 and/or arms 110 and 112.

In some embodiments, the oral insert 102 may comprise a light source 282 embedded therein to provide high contrast and accuracy during scanning thereof.

In some embodiments, the fiducial element 100 may be configured in any suitable manner. Some exemplary configurations are shown in FIGS. 7A-7C, it being appreciated that many other suitable configurations may be realized.

Figures 7A, 7B, 7C:
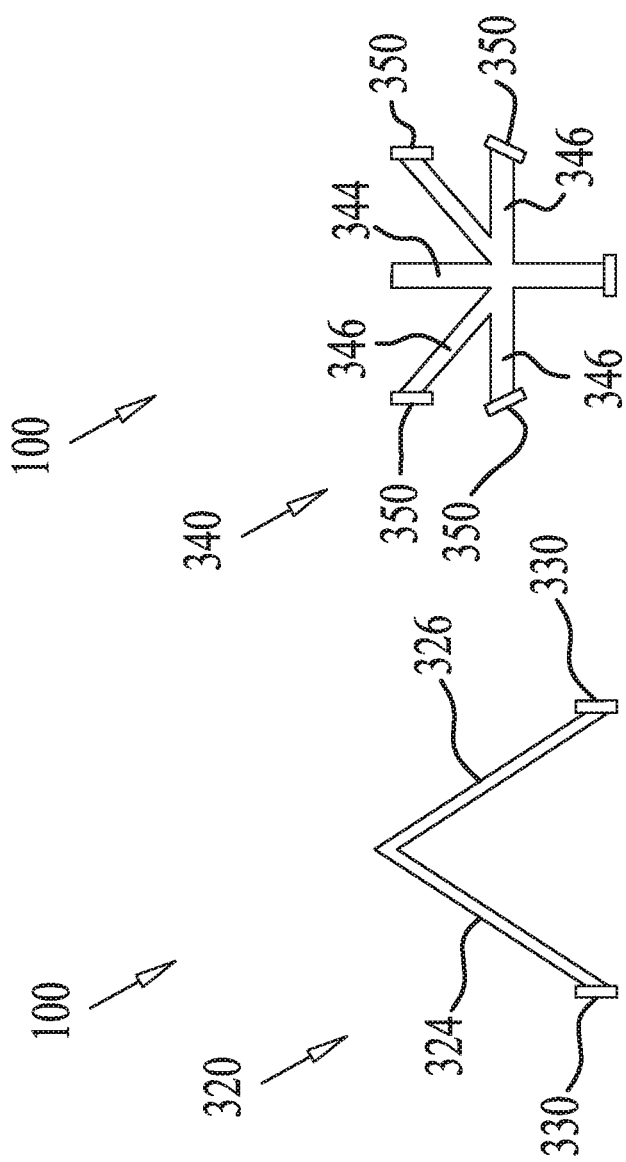
FIGS. 7A-7C are each a simplified schematic illustration of a fiducial element according to some embodiments of the present disclosure.

As seen in FIG. 7A, the fiducial element 100 comprises an oral insert 300. The oral insert 300 may be formed in a generally Y-like shape, comprising a central rod 302 and arms 304 and 306. Plates 310 may be placed at edges of any one of rod 302, and arms 304 and 306. The plates 310 may be formed with characters 128 (FIGS. 2 and 3). The oral insert 300 may be placed at any suitable location within the oral cavity 114 and the scanning thereof may be performed as described in reference to FIGS. 4 and 5.

As seen in FIG. 7B, the fiducial element 100 comprises an oral insert 320. The oral insert 320 may be formed in a generally V-like shape, comprising arms 324 and 326. Plates 330 may be placed at edges of any one of arms 324 and 326. The plates 330 may be formed with characters 128 (FIGS. 2 and 3). The oral insert 320 may be placed at any suitable location within the oral cavity 114 and the scanning thereof may be performed as described in reference to FIGS. 4 and 5.

As seen in FIG. 7C, the fiducial element 100 comprises an oral insert 340. The oral insert 340 may be formed of a central bar 344 and a plurality of arms 346 extending therefrom. Plates 350 may be placed at edges of any one of bar 344 and arms 346. The plates 350 may be formed with fiducial markers 128 (FIGS. 2 and 3).

The oral insert 340 may be placed at any suitable location within the oral cavity 114 and the scanning thereof may be performed as described in reference to FIGS. 4 and 5. The plurality of arms 346 and/or plates 350 may provide for a plurality of fiducial markers, thus enhancing the scanning accuracy and allowing for securely placing the oral insert 340 within the oral cavity 114.

Figure 8:
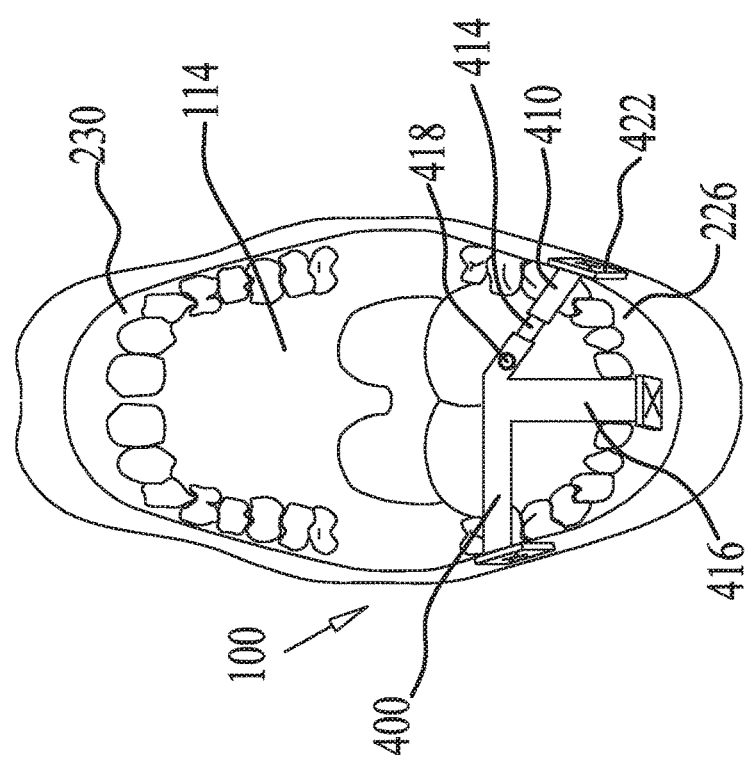
FIG. 8 is a simplified schematic illustration of a fiducial element within an oral cavity at an open state, according to some embodiments of the present disclosure.

FIG. 8 is a simplified schematic illustration of a fiducial element 100 within the oral cavity 114 at an open state. As seen in FIG. 8, the fiducial element 100 comprises an oral insert 400 formed with at least one lengthwise adjustable arm 410. The arm 410 may comprise an elastic portion, a spring, or any other extendable portion 414. In some embodiments, the arm 410 may be rotatable, or in any way movable, respective to a central bar 416. The adjustable oral insert 400 allows for fitting the oral insert 400 with the particular size and shape of the oral cavity 114. In some embodiments, an indicator may be provided to measure the location of the rotatable arm 410 in respect to a fiducial marker. Such an indicator may be an encoder operative to measure a distance and/or an angle between the rotatable arm 410 and a fiducial marker. Additionally or alternatively, an optical scan of an indicating portion of the oral insert 400 (such as a scale, a digital readout, or simply portion of the geometry itself such as an angle or a length of an adjustable arm portion) is used for determination of the actual distance affecting fiducial mark positions. For example, scanning the length of just extendible portion 414 potentially allows determining the current distance between a fiducial target on plate 422 and other fiducial targets of the oral insert 400. Optionally, the plate 422 is adjustable to fit at a particular location relative to a scan field recommended by a scan protocol, for example, to achieve good field overlap between a fiducial scan image and a corresponding standard scan image.

In some embodiments, the adjustment of the adjustable oral insert 400 to the oral cavity 114 may be performed by a length measurement device, such as an optical encoder 418 embedded in the adjustable oral insert 400. The optical encoder 418 may measure the distance required for adjusting the arm 410 to the arch 204 for placing a plate 422 fittingly on an outer side of the mandible 226. The measured distance may be transmitted to the processing unit and accordingly the adjustment of the adjustable oral insert 400 to the arch 204 is performed. It should be understood that the adjustment, once made, provides a new distance which may be rigidly held by the fiducial element at least for the duration of the fiducial scanning.

Figure 9:
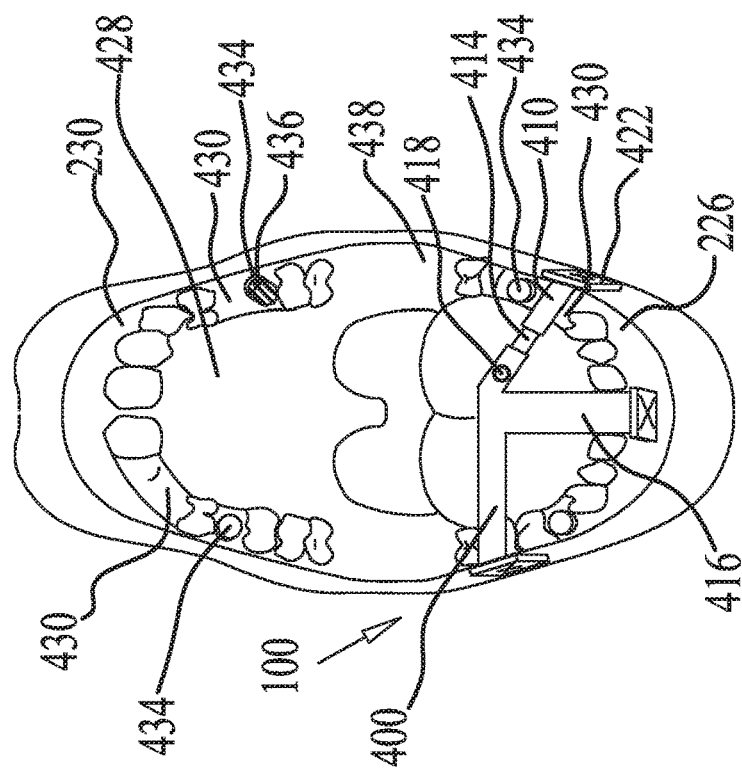
FIG. 9 is a simplified schematic illustration of a fiducial element within an oral cavity at an open state, according to some embodiments of the present disclosure.

Turning to FIG. 9, it is seen that an oral cavity 428 is partially edentulous. In some locations 430 the gingiva is exposed. In some location a conventional implant 434 is inserted in place of the missing tooth. Accurate scanning by an intraoral scanner of a fully or partially edentulous oral cavity 428 can be challenging, since the teeth structure at exposed locations 430 and at implant locations 434 is discontinuous, and the scanning error along the designated arch, may accumulate. For example, the accumulated error of the arch 204 may be up to about 0.6 mm, in a non-limiting example, while the accumulated error of the same area in a dentate oral cavity 114 may be, in a non-limiting example, about 0.038-0.333 mm.

Accurate scanning of the edentulous oral cavity 428 is important, since the measurements for a location on the arch designated for a future implant should be accurate. This is since implants, unlike teeth, may have a lower degree of mobility along the jawbone relative to the teeth.

In some embodiments, in order to generate a digital impression of the implants 434 a "scannable abutment" 436 may be placed and located on top of the implant 434. The scannable abutment 436 bottom may be scanned by the intraoral scanner and the intraoral scanning algorithm may replace the abutment 436 with the dimensions of a top portion of the implant 434. This is a potential advantage since the implant 434 is optionally metallic and therefore its surface is highly specular and more difficult to scan. In some embodiments, the scannable abutment 436 is designed to be scanned by the intraoral scanner from the top, at a 45° angle, or in some embodiments, from the side. In some embodiments, the scannable abutment 436 comprises a non-specular surface, for example a ceramic, composite and/or polymer surface). In some embodiments, the scannable abutment 436 is formed with a non-smooth geometry (bumped, dimpled, engraved, and/or otherwise roughened) that provides a potential advantage by providing suitable surface features for use in registration. In an embodiment, there may be provided an abutment which protrudes sufficiently from the implant that it can be accurately located (scannable) even when scanned from the side only. To improve the accuracy of locating the abutment, its buccal side 438 can be marked or engraved with fiducials or markers as described herein.

According to some embodiments, a fiducial element 100, such as an oral insert, is optionally used to provide a fiducial marker to mark a reference point within the edentulous oral cavity 428. Exemplary oral inserts are shown in FIGS. 9-15, it being appreciated that many oral insert configurations may be realized.

As seen in FIG. 9, the oral insert 400 may be placed within the edentate oral cavity 428. The arm 410 may be extended to cover the exposed locations 430 on the mandible 226, thus providing a fiducial marker at the location prone to cause scanning inaccuracies. During fiducial scanning, such as described in FIGS. 4A-4B, a plurality of scans may be performed wherein during each scan the arm 410 may be moved to extend over another desired location. It should be understood that the resulting change in fiducial feature geometry at each position is recorded and used in geometrical reconstruction of the oral arch. In the example of FIG. 9, during a first fiducial scan the arm 410 may extend over exposed locations 430, as seen in FIG. 9. Thereafter, the arm 410 may be moved to extend over implant location 434 and an additional scanning thereof may be performed and further processed.

The optical encoder 418 may be provided to measure the distance and angle required for adjusting the arm 410 to the arch 204 for placing the arm 410 over the desired location, (such as locations 430 or 434) and plate 422 fittingly on an outer side of the mandible 226.

Figure 10:
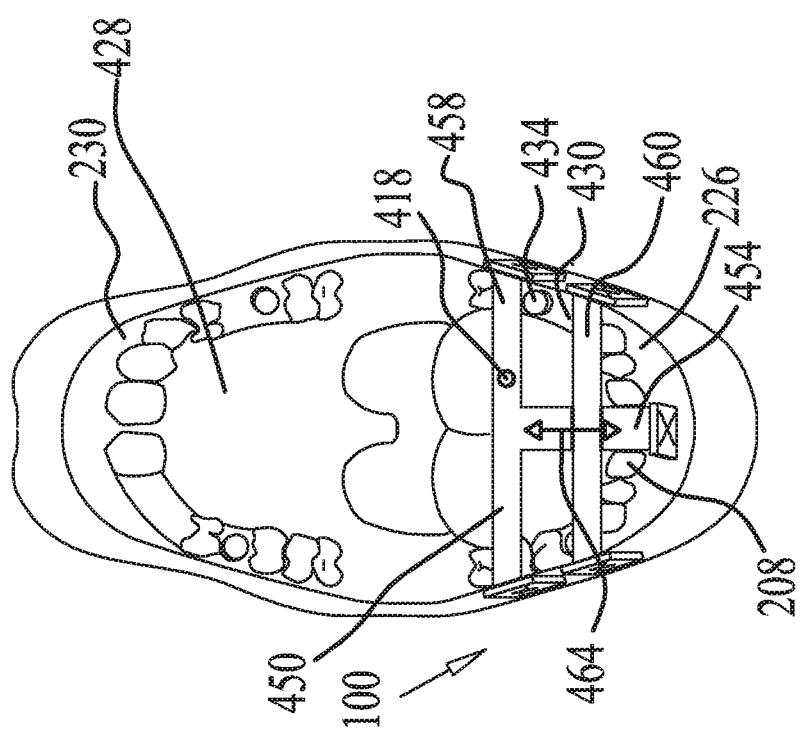
FIG. 10 is a simplified schematic illustration of a fiducial element within an oral cavity at an open state, according to some embodiments of the present disclosure.

Turning to FIG. 10, another exemplary oral insert 450 is shown at least partially placed within edentulous oral cavity 428. The oral insert 450 may comprise a central rod 454 which may be generally immovably placed on the mandible 226. A distal arm 458, distal in respect to lower incisor 208, may be generally immovably placed on the mandible 226. A proximal arm 460 may be movable along the central rod 454 in the orientation of arrow 464. Accordingly, during fiducial scanning, such as described in FIGS. 4A-4B, at a first fiducial scan the proximal arm 460 may extend over exposed locations 430, as seen in FIG. 10. Thereafter, the proximal arm 460 may be moved distally to extend over implant location 434 and an additional scanning thereof may be performed and further processed. In some embodiments, the distal arm 458 and/or the central rod 454 may be movable in any suitable orientation. In some embodiments, the proximal arm 460 may be immovable.

Figure 11:
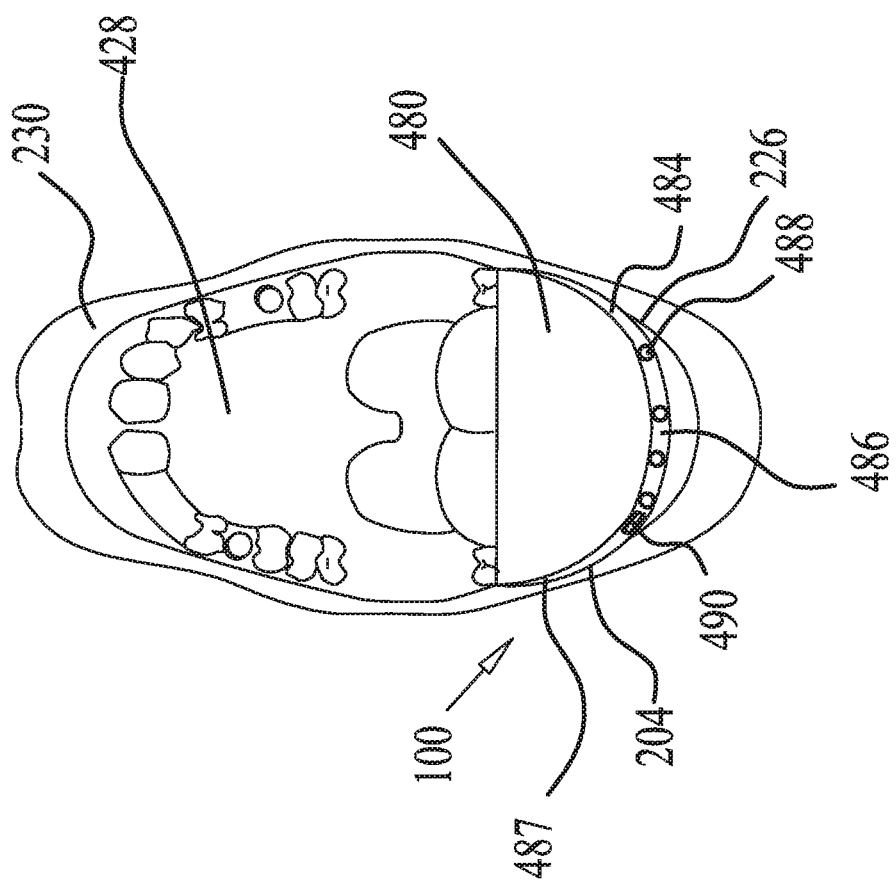
FIG. 11 is a simplified schematic illustration of a fiducial element within an oral cavity at an open state, according to some embodiments of the present disclosure.

As seen in FIG. 11, an oral insert 480 may be configured generally as a partial or full arch shape. At an outer thickness surface 484 thereof there may be placed fiducial marks 488. The fiducial marks 488 may comprise a barcode, a character (such as character 128 of FIGS. 2 and 3), for example. During scanning the oral insert 480 may be placed intermediate the maxilla 230 and mandible 226, wherein a closed state. The designated full or partial arch 204 may be scanned from the side including all teeth and implants abutments.

In some embodiments the outer thickness surface 484 may be in the range of approximately 0.3-15 mm, or in the range of approximately 1-5 mm or any suitable size. In some embodiments the thickness may vary. For example the thickness at a front portion 486 on the surface 484 may be greater than at a side portion 487 thereof. In a non-limiting example, the thickness at the front portion 486 may be about 3 mm and the thickness at the side portion 487 may be about 1 mm.

In some embodiments, light sources 490 such as LEDs may be embedded within outer thickness surface 484 or any other suitable location. The light sources 490 may provide high contrast and accuracy during fiducial scanning. Masks may be added over the LEDs to provide additional degree of distinction of the features.

Figure 12:
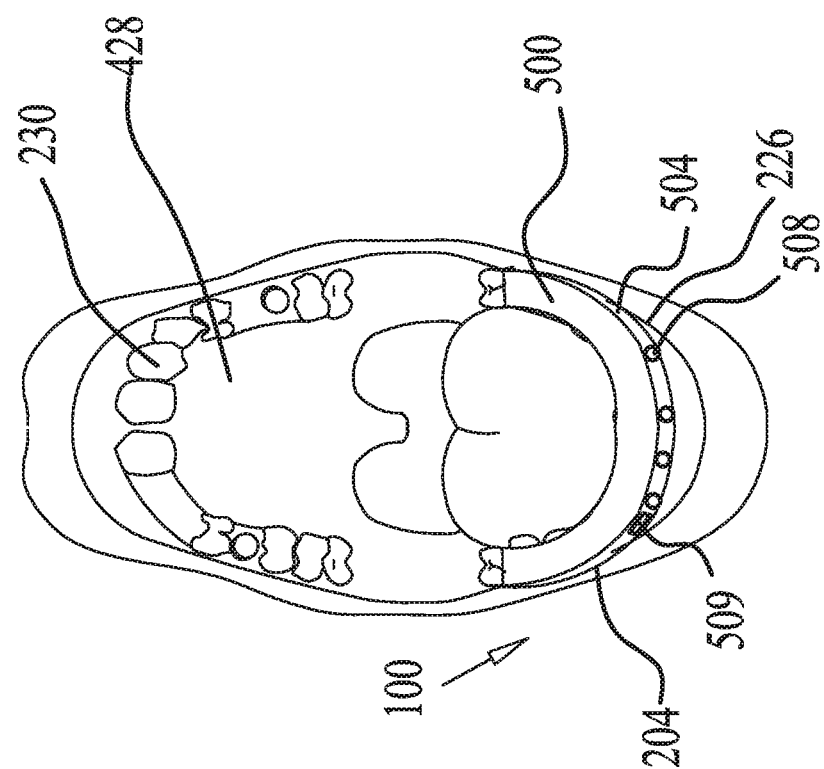
FIG. 12 is a simplified schematic illustration of a fiducial element within an oral cavity at an open state, according to some embodiments of the present disclosure.

Turning to FIG. 12, it is seen that an oral insert 500 may be configured generally in a semi-annulus shape. At an outer thickness surface 504 thereof there may be placed fiducial marks 508. The fiducial marks 508 may comprise a barcode, a character, for example. Optionally, the marks are etched and/or embossed, allowing their identification from geometry information alone. Optionally, the marks are printed or otherwise placed to alter surface reflectance properties. During scanning, the oral insert 500 may be placed intermediate the maxilla 230 and mandible 226, which are in a closed state. The designated full or partial arch 204 may be scanned from the side including all teeth and implants abutments. It should be noted that FIG. 12 comprises an example of an oral insert having an alternative fiducial marking configuration to "plates", as described, for example, in relation to FIGS. 1-3.

Figure 18:
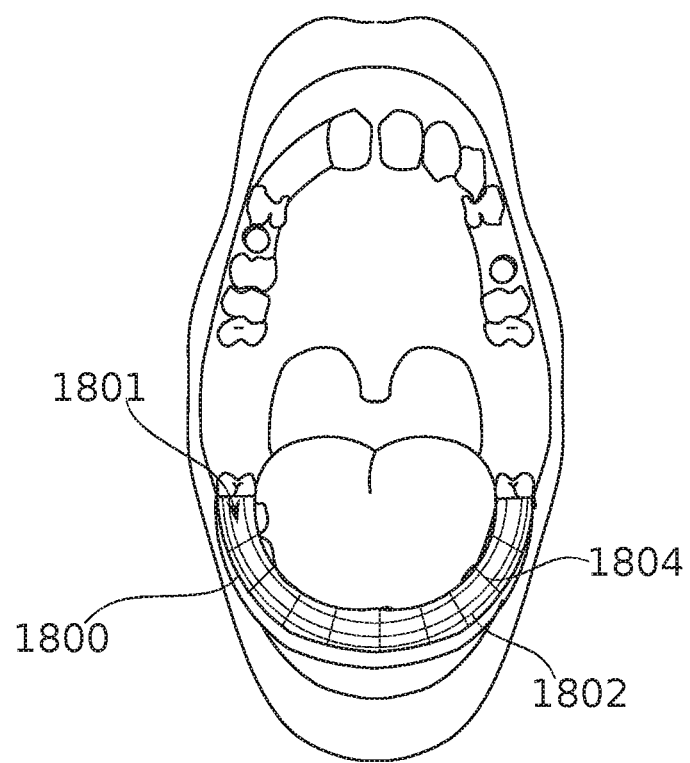
FIG. 18 schematically illustrates an oral insert having fiducial markings along a surface facing the occluding surface of an oral arch, according to some embodiments of the present disclosure.

Reference is now made to FIG. 18, which schematically illustrates an oral insert 1800, having fiducial markings 1802, 1804 along a surface 1801 facing the occluding surface of an oral arch, according to some embodiments of the present disclosure.

Optionally, fiducial features 1802, 1804 (contour lines 1802 and radial marks 1804 are shown as examples) are placed along the occluding surfaces of the oral insert 1800. More lingual and/or tooth-overlying portions of the fiducial features 1802, 1804 are optionally observed when the mandible and maxilla are separated. Optionally, the occlusal surface facing surfaces 1801 extend buccally from the oral insert 1800 so that at least a portion of the occlusal surface fiducial features 1802, 1804 is visible. A potential advantage of this configuration is to bring tooth crown and fiducial element features into close proximity. In some embodiments, a fiducial feature comprises a contour line 1802, optionally a concentric group of contour lines, extending along and around a crown surface of the oral insert 500. The contour line or lines are engraved, embossed, or printed, for example. A potential advantage of such a feature is to allow direct determination of the distance between crown end and fiducial feature. This can be useful, for example, in isolating the positions of scan registration errors in the original reconstruction. Optionally, the contours are shaped to approximate a standard jaw structure. Optionally, this is used, for example, together with the method of jaw structure model usage described in relation to block 266 of FIG. 5A, herein. Optionally, radially oriented lines 1804 (and/or other markings) are used to help determine distance along lines 1802.

In some embodiments, light sources 509, such as LEDs, may be embedded within outer thickness surface 504 or any other suitable location. The light sources 509 may provide high contrast and accuracy during fiducial scanning. Masks may be added over the LEDs to provide additional degree of distinction of the features (for example, the fiducial marks are optionally constituted not merely as reflectance surface properties, but as light-emitting regions).

Figure 13:
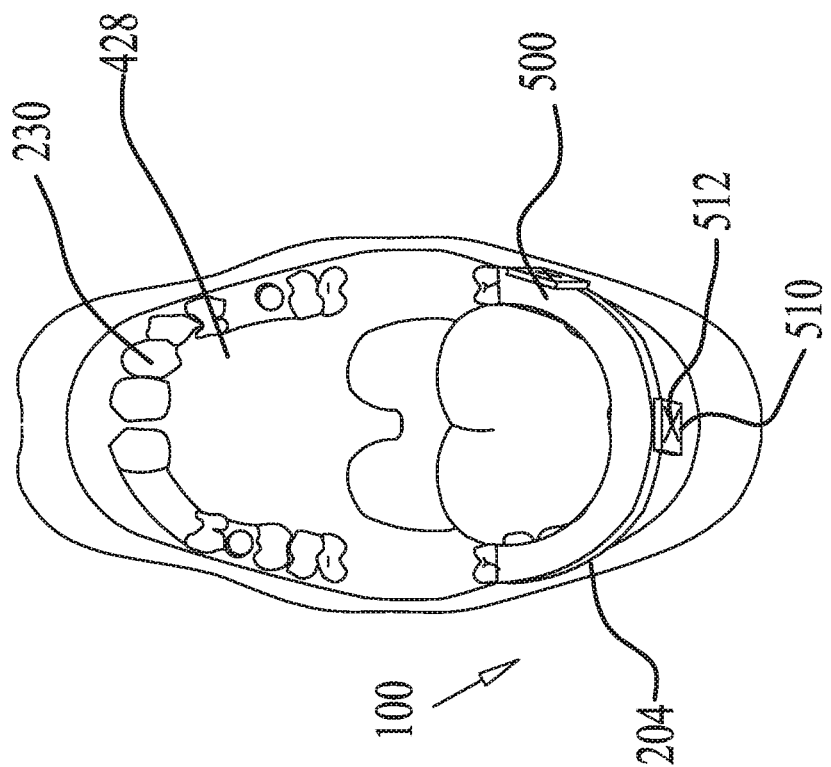
FIG. 13 is a simplified schematic illustration of a fiducial element within an oral cavity at an open state, according to some embodiments of the present disclosure.

As seen in FIG. 13, the oral insert 500 may be provided with plates 510, which may also comprise fiducials markers 512, which may be scanned as described in reference to FIGS. 4 and 5. During fiducial scanning, the plates 510 may be scanned with teeth and abutments or implants in between the plates 510.

Turning to FIG. 14 it is seen that oral insert 500 may be provided with a continuous strip 520 surrounding at least a portion of the outer thickness surface 504. In some embodiments the thickness of strip 520 may be in the range of approximately 1-7 mm, or any suitable size. Strip 520 may comprise fiducial markers 522. The strip 520 and/or fiducial markers 522 may be scanned as described in reference to FIGS. 4 and 5. A potential advantage of such a strip is to provide a continuous region of well-determined geometry, for example, to continuously fill in a large gap between teeth.

In the embodiments of FIGS. 1-14, the fiducial markers are shown placed at external (buccal) surface 232 of the teeth. Additionally or alternatively, the fiducial markers may be placed within the oral cavity at an internal surface 540 of the teeth, such as shown in FIG. 15. An oral insert 550 may be formed with a central T-like bar 556 and extendable arms 560, 562 and 564 extending therefrom and can fix the oral insert to the jaw. In some embodiments the fiducial markers may be provided as plates 570 and 572, and 574 placed at edges of respective arms 560 and 562 and 564 up and against the internal surface 540 of the arch 204. In some embodiments, the fiducial markers may be provided as characters 580 etched, embossed, and/or in any other suitable manner marked, on arms 560, 562 and 564. Plates 570, 572 and 574 may or may not be obviated in such embodiments.

The extendable arms are configured to be adjusted to abut against the internal surface 540 of the teeth. In some embodiments, this may be performed by an optical encoder 582 embedded in the oral insert 550. The optical encoder 582 may measure the distance required for adjusting any one of the arms 560, 562 and 564 to the arch 204 for placing the plates 570, 572 and 574 or edges of the arms 560, 562 and 564 fittingly at internal surface 540. The measured distance may be transmitted to the processing unit and accordingly the adjustment of the adjustable oral insert 550 to the arch 204 is performed.

The arms 560, 562 and 564 may comprise an elastic portion, a spring, or any other extendable portion (however, in situ, adjusted to press against the oral arch, it should be understood that the distances established between fiducial marks are rigidly held to allow them to be precisely determined). In some embodiments, the arms 560, 562 and 564 may be rotatable, or in any way movable, respective to a central T-like bar 556. The oral insert 550 may be shaped in any suitable form, such as described in reference to FIGS. 1-14, while the fiducial marker is placed within the oral cavity at the internal surface 540 thereof.

The oral insert 550 may be placed upon the arch 204 of the mandible 226, as shown in FIG. 15, or may be placed upon the arch 204 of the maxilla 230.

Scanning of the oral insert 550 and processing the data received therefrom may be formed by scanning method 200 and data processing method 250, such as described in the flowchart of FIGS. 4 and 5, mutatis mutandis, as will be described as follows. It should be understood that elucidating remarks made herein applying to the descriptions of FIGS. 4 and 5 also apply, changed as necessary, to corresponding portions of the following descriptions.

As seen in FIG. 4A, at block 202, the initial standard scan of the designated full or partial arch 204 is performed by intraoral scanning methods. Typically, the scanning is performed by using a handheld scanner including optical sensors for capturing a 3-D dataset of the designated full or partial arch 204.

The fiducial element 100 comprising oral insert 550 may be inserted at any suitable location within the oral cavity 114, as seen at block 222. In FIG. 15 the oral insert 550 is shown placed upon the mandible 226 resting on the tongue 228. The plates 570, 572 and 574 or edges of the arms 560, 562 and 564 are placed at internal surface 540 of the teeth.

Once the fiducial element 100 is fixedly placed within the oral cavity 114, fiducial scanning of the arch 204 is performed, as seen in block 234, while the oral cavity 114 is in an open state. The fiducial scanning may be performed in any suitable manner, such as by the same intraoral scanning method used for the standard scanning of block 202. For example, 3-D scanning of each of the fiducial markers, such as plates 570, 572 and 574 or edges of the arms 560, 562 and 564, may be performed such that each plate or arm edge is scanned along with character or fiducial marker 580 and a surrounding area of uncovered teeth. The fiducial scanning may be of each of the plates or arm edge and a surrounding area without requiring scanning of the complete designated arch. In the example of FIG. 15, three fiducial scans may be performed: one of plate 570 and surrounding area, one of plate 572 and surrounding area and one of plate 574 and surrounding area. This fiducial scanning may be very short, such as a few seconds to a few minutes long.

In some embodiments, block 234 is performed additionally on the maxilla 230. In some embodiments, the accuracy correction may be transferred from the mandible 226 to the maxilla 230 or vice versa by 3-D scanning of an area including both the mandible 226 and the maxilla 230.

In some embodiments, upon completion of the fiducial scanning of block 234, a small area, such as plate 570 or edge of arm 560, may be rescanned to ensure the fiducial markers did not inadvertently move during the fiducial scanning.

As seen in block 238, the oral insert 550 may be removed from the oral cavity 114.

Thereafter, as seen in block 240, received data from the initial standard scanning of block 202 may be processed with received data from the fiducial scanning in any suitable manner.

An exemplary processing method 250 is shown in the flowchart of FIG. 5A.

As seen in FIG. 5A, a processing unit may be used along with data connection to the intraoral scanner to perform the following:

As seen in block 254, an algorithm is executed for matching the teeth scanned in each of the fiducial scanning with the teeth scanned in the initial standard scanning of block 202.

In block 258, the 3-D location of each of the fiducial marker, such as plates 570, 572 and 574 or edges of the arms 560, 562 and 564 and/or the characters 580 thereof, is identified relative to a resultant configuration from the initial standard scanning.

At block 260, an optimal transformation of the reference fiducial configuration towards the resultant configuration is calculated and applied upon the reference configuration.

At block 262, an optimal transformation of each of the fiducial scans towards the modified reference configuration is evaluated and applied.

At block 264, the optimal transformation of matched teeth of initial standard scanning towards the transformed fiducial scans is evaluated.

At block 266, the optimal transformation of the teeth of block 264 may be applied to the data received during the initial standard scanning of block 202. In some embodiments, block 266 may be performed with the aid of conventional jaw structures model data.

Following block 266, a resultant configuration and model of the designated full or partial arch 204 is provided, as seen in block 270.

Figure 16:
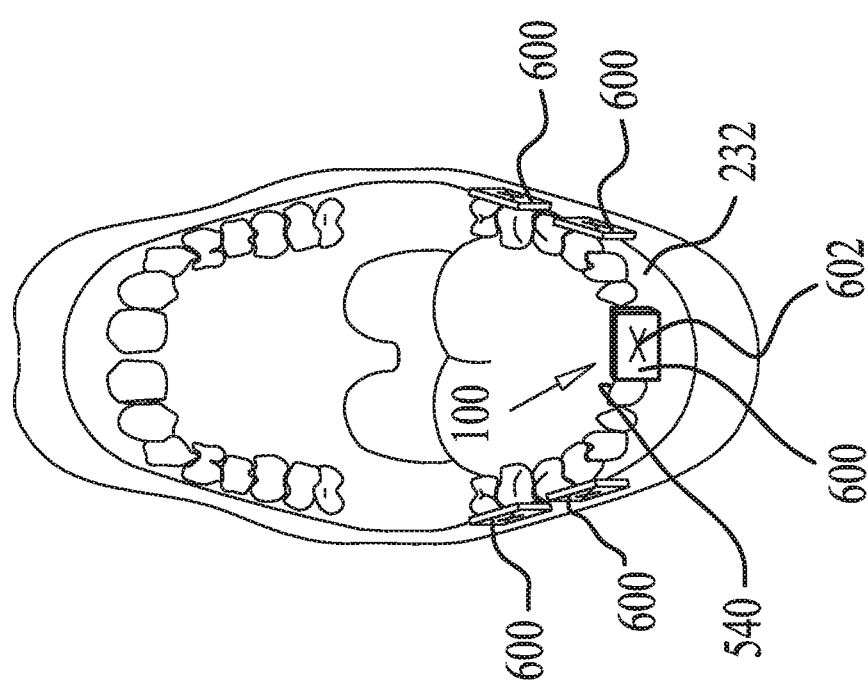
FIG. 16 is a simplified schematic illustration of a fiducial element within an oral cavity at an open state, according to some embodiments of the present disclosure.

In the embodiments of FIG. 1-15 the fiducial element 100 comprises an oral insert. In some embodiments, the fiducial element 100 may comprise fiducial markers formed by plates 600 and/or by characters 602 marked thereon, as shown in FIG. 16. The plates 600 may be placed at any suitable location within the oral cavity 114, at the external surface 232 or internal surface 540. The plates 600 may be fixed to the teeth or oral cavity 114 in any suitable manner, such as by an adhesive, or suction, for example. The plates 600 may be formed in any suitable configuration, such as metal plates, sheets and adhesives, for example.

To ensure accurate measurement, a fixed location may be measured, such as some fixed location within the oral cavity. The distance between the fiducial markers on plates 600 and the fixed location can be used as a measurement for correcting any accumulated inaccuracies accruing during the intraoral scanning of the oral cavity. Such embodiments provide a potential advantage for cases where relatively long-term fiducial stability is indicated. For example, the fiducial marks can be used to provide stable spatial references during the configuration of a configurable abutment. Optionally, the 3-D locations are measured based on imaged acquired by a stereo camera, or by a standard camera from two or more directions.

In some embodiments, such as the embodiments of FIGS. 1-16, the fiducial element 100 may be covered by a coating and/or layer of flexible material designed to provide enhanced fixation and stability of the fiducial element 100 by the jaws at closure of the oral cavity 114. The flexible material layer provides additional contact points between the jaw and the fiducial element 100. Without the flexible material layer there might be only a few contact points between the jaws and the fiducial element 100.

The flexible material layer may be formed such that when pressed by the teeth, it allows the teeth to imprint into the flexible material layer while maintaining a desirable degree of stiffness, to keep fiducial element 100 fixed relative to the jaws at an accuracy of around 20 μm, around 30 μm, around 100 μm, or any other suitable (greater, smaller, or intermediate) degree of accuracy.

In some embodiments, the flexible material layer can have thickness of 0.1-2 mm, for example. In some embodiments the flexible material layer can have a larger thickness, when the layer is sufficiently stiff. In some embodiments the flexible material layer can be configured to cover only the possible occluded contact area of teeth.

Figure 17A:
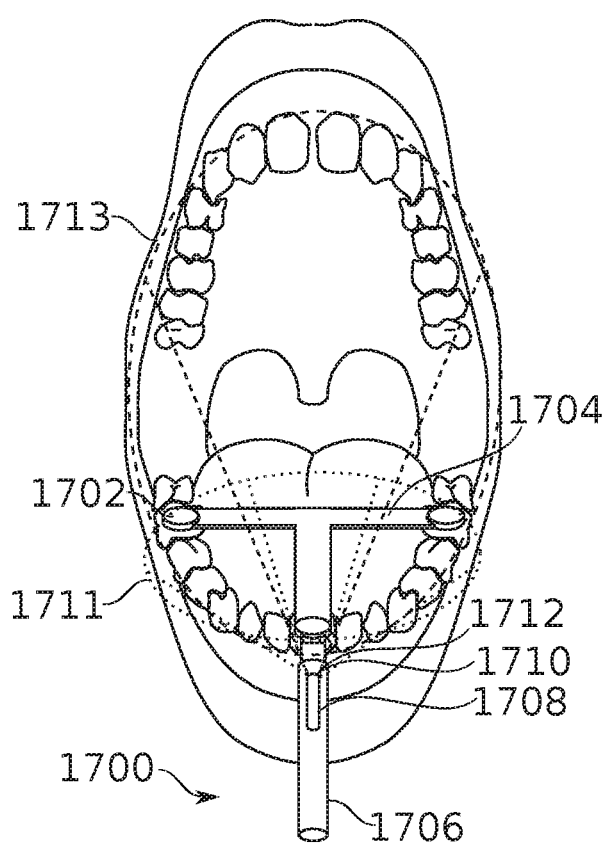
FIGS. 17A-17B schematically illustrate a fiducial element with integrated scanning device, according to some embodiments of the present disclosure.
Figure 17B:
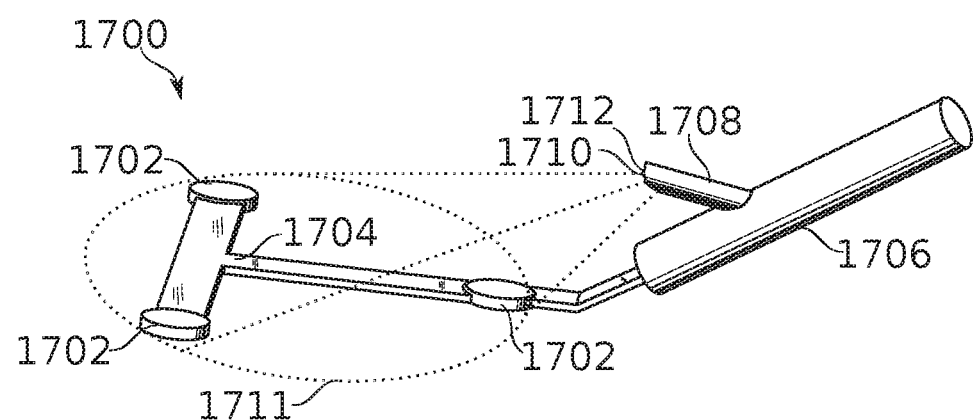

Reference is now made to FIGS. 17A-17B, which schematically illustrate a fiducial element 1700 with integrated scanning device 1710, according to some embodiments of the present disclosure.

In some embodiments, a fiducial element 1700 comprises a plurality of fiducial targets 1702, interconnected by an interconnecting element 1704. Shown is T-shaped interconnecting element 1704; it should be understood that any other interconnecting element shape is optionally provided, for example as such shapes are described in relation to the figures herein.

In some embodiments, fiducial element 1700 additionally comprises a scanning camera 1710, optionally along with a scanning illumination source 1712. To give a suitable scanning field of view 1711, the scanning camera 1710 and/or illumination source 1712 are held out of the plane of fiducial targets 1702 by one or more portions of fiducial element 1700, for example, by interconnecting element 1704, handle 1706, and/or mount 1708. Optionally, a field of view 1713 is provided which is large enough to encompass both the mandible and maxilla. Optionally, the device is used against the mandible, and/or against the maxilla.

In some embodiments of the invention, the spatial relationship of the camera 1710 to the fiducial marks 1702 is known according to the geometrical configuration of the fiducial element 1700. For example, the relationship is fixed, or adjustable with a scale or other measurable indication. By imaging the fiducial marks in relation with the teeth, data is acquired which can be registered to other intraoral scan data, allowing scan data position constraints (for example, error correction) to be applied in a computer reconstruction of the oral 3-D geometry.

In some embodiments, fiducial targets 1702 each comprise a contact sensor. Optionally, image acquisition by camera 1710 is coupled to activation of the contact sensors. In some embodiments, the camera is triggered by contact of at least two contact sensors. In some embodiments, contact by two, three, or more sensors is required. Optionally, the number of contacts required for triggering is configurable, for example, based on the configuration of the teeth in the jaw of the patient (two contacts used when teeth are missing that would be underneath a third contact, for example). In some embodiments, triggering comprises identification, and optionally recording, of the contact sensor(s) which trigger image acquisition.

Contact triggering is a potential advantage to help ensure that the fiducial targets 1702 are in a known spatial relationship (comprising contact at some point) with elements of the oral arch. Another potential advantage of contact triggering is to the speed and facility of automatic image acquisition while using one hand.

Figure 19:
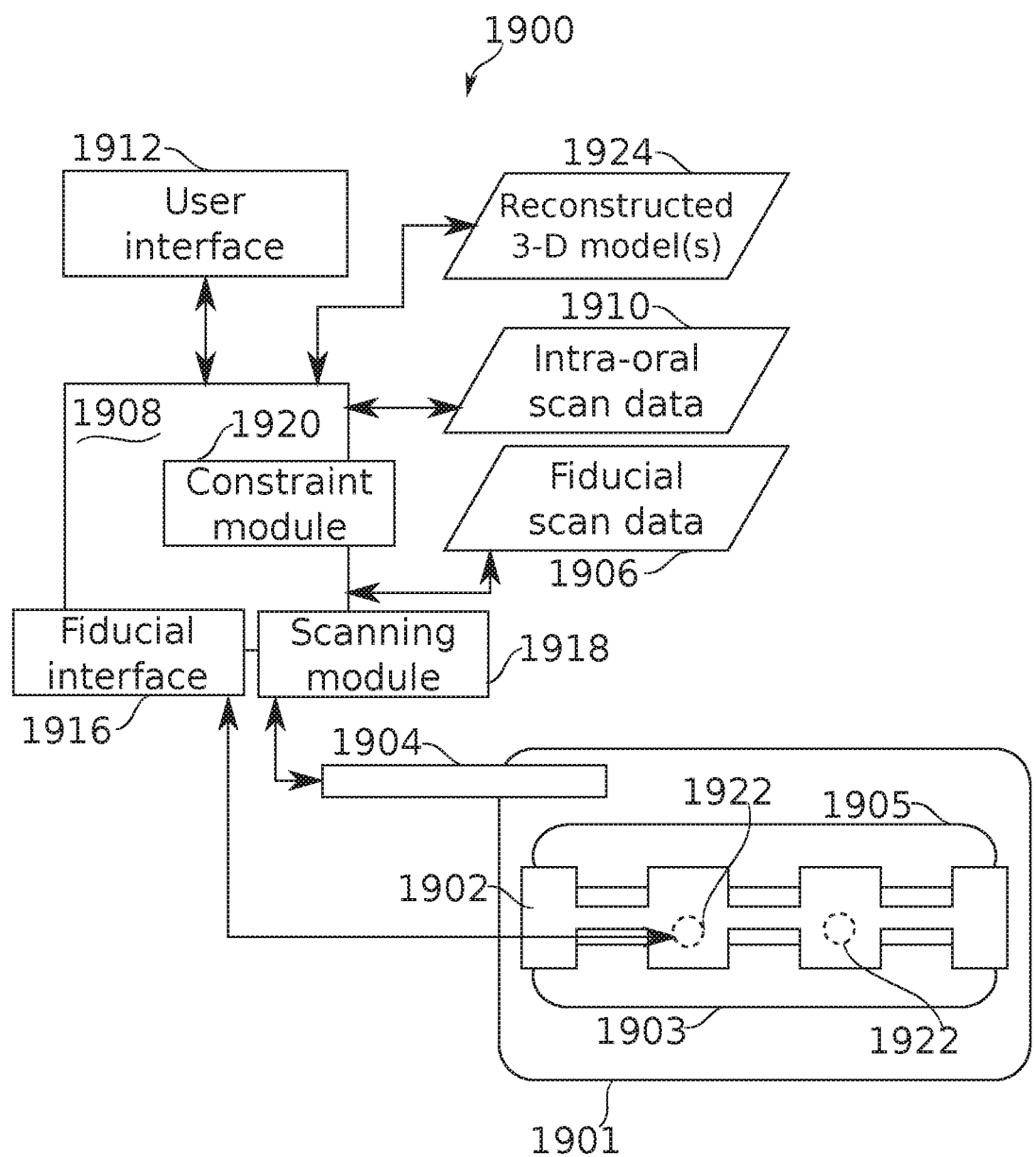
FIG. 19 schematically illustrates a system for constraining the geometrical reconstruction based on intraoral scan data, according to some embodiments of the present disclosure.

Reference is now made to FIG. 19, which schematically illustrates a system 1900 configured to constrain geometrical reconstruction from intraoral scan data 1910, 1906 (for example, to correct reconstruction inaccuracies) using a fiducial element 1902, according to some embodiments of the present disclosure.

System elements are shown in highly schematic form. In some embodiments, a fiducial element 1902 is provided for insertion to an oral cavity 1901; it is optionally held, for example between oral arches 1905 and 1903.

In some embodiments, a processing module 1908 is provided (which comprises, for, example, one or more digital computers). Optionally, module 1908 comprises one or more sub-modules (which comprise be hardware and/or software sub-modules). Optionally, the modules include fiducial element interface 1916, scanning module 1918, scan constraint module 1920, and/or user interface module 1912.

In some embodiments, oral scans are obtained (with and/or without the fiducial element 1902 in place) using scanner wand 1904. Optionally, scanning module 1918 supervises acquisition and/or initial stitching (or other reconstruction) of scan data into a 3-D model of oral geometry. For convenience of reference, scan data acquired without a fiducial element 1902 in place are represented as intra-oral scan data 1910; scans acquired with the fiducial element in place are represented as fiducial scan data 1906.

In some embodiments, a fiducial element 1902 comprises one or more electronic devices 1922 (for example, position sensing encoders, contact sensors, LEDs, and/or camera/scanner hardware). Optionally, fiducial interface module 1916 communicates with these devices; for example, to control power, manage operation, and/or detect signals.

In some embodiments constraint module 1920 processes scan data 1910, 1906; optionally in coordination with data obtained via fiducial interface 1916, to apply geometrical correction and/or constraints to optical scan data 1910 in order to produce and/or modify a reconstructed model of oral geometry 1924. Optionally, one or both of an unconstrained (direct-from-scan) and constrained (optionally, corrected) 3-D model is created.

In some embodiments user interface 1912 is used for control of and/or display from processing module 1908. In particular, interface control/display is optionally exercised over any of the processing module 1908 sub-modules 1920, 1916, 1918.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A fiducial element providing fiducials for geometrical constraint of optical intraoral scan data in reconstruction of oral arch geometry from the optical intraoral scan data, the fiducial element comprising:

an oral insert which removably fits into a mouth, and is shaped to extend over an occlusal surface of an oral arch to rigidly interconnect at least three fiducial features, the fiducial features being distributed over an extent of the oral arch of at least eight tooth positions;

wherein:

at least one of the three fiducial features is carried on an at least one plate positioned and oriented to extend at least partially over a facial surface of a tooth or at least partially over where a facial surface of a tooth would be in a complete oral arch for a missing tooth, when the oral insert is in the mouth;

the oral insert is shaped as an insert with at least one arm and at least one of the fiducial features is positioned near an end of the arm;

at least one of a length of the arm and an angle of the arm is adjustable; and the fiducial element comprises at least one of:

an electronic encoder configured to measure at least one of said length of said arm and said angle of said arm; and a marked scale.

2. The fiducial element of claim 1, wherein the fiducial features are located at least two tooth positions apart from each other, along the oral arch, when the oral insert is in the mouth.

3. The fiducial element of claim 1, wherein said at least one of the at least three fiducial features is positioned against a facial tooth surface on the buccal side of the oral arch, when the oral insert is in the mouth.

4. The fiducial element of claim 1, wherein at least one of the at least three fiducial features is positioned on a surface of the fiducial element which extends over the occlusal surface of the oral arch, when the oral insert is in the mouth.

5. The fiducial element of claim 1, wherein the insert is shaped to be held by clamping between jaws of the mouth; and at least one plate is shaped and positioned to extend over a portion of both maxillary and mandibular oral arches of the jaws when the insert is held between the jaws.

6. The fiducial element of claim 1, wherein the at least one plate is at least 5 mm wide along the extent of the oral arch.

7. The fiducial element of claim 1, wherein the at least three fiducial features are held on at least three corresponding plates, and the plates are separated from each other by at least two tooth positions.

8. The fiducial element of claim 1, wherein the oral insert is formed with an outer layer of flexible material at a region where the rigid interconnections cross an oral arch when the oral insert is in the mouth, the layer of flexible material being configured to elastically deform when clamped between jaws of the mouth to fix the oral insert in position.

9. The fiducial element of claim 1, wherein the oral insert comprises at least one LED.

10. The fiducial element of claim 1, wherein the oral insert comprises an arcuate surface positioned and shaped to face an occlusal surface when held between occlusal surfaces of a maxilla and a mandible when the oral insert is in the mouth; and wherein the fiducial features comprise at least one contour line extending along the arcuate surface and at least partially lingual or buccal to the oral arch when the oral insert is in the mouth.

11. The fiducial element of claim 10, wherein the oral insert also comprises a surface facing buccally from the oral arch when the oral insert is in the mouth; and wherein the surface facing buccally comprises at least one of the fiducial features.

12. The fiducial element of claim 1, wherein the fiducial features are rigidly interconnected to distances determined with an offset smaller than 30 μm.

13. The fiducial element of claim 1, comprising:

and imaging camera and a light collection aperture of the imaging camera, oriented to collect imaging light from the fiducial features;

wherein the fiducial features and the light collection aperture are rigidly interconnected to determined positions with respect to one another.

14. The fiducial element of claim 13, comprising a plurality of contact sensors positioned on the oral insert to contact teeth when the insert is fitted into the mouth, wherein imaging by the imaging camera is activated upon contact being sensed by least two of the plurality of contact sensors.

15. The fiducial element of claim 1, provided as part of a system for reconstructing oral geometry using optical intraoral scanning, wherein the system further comprises a geometry constraint module including a processor, and a memory storing non-volatile computer instructions which, upon execution, operate the processor to:

receive optical scan data from a plurality of oral regions;

receive fiducial scan data comprising scans of the rigidly interconnected fiducial features of the fiducial element, each positioned adjacent to a portion of the plurality of oral regions; and determine the relative positions of the plurality of oral regions based on dimensions of the rigid interconnections of the fiducial features, and on the positions of the fiducial features relative to each corresponding adjacent oral portion.

16. The system of claim 15, wherein at least one of the dimensions of the rigid interconnections is provided to the constraint module by a fiducial interface in communication with an encoder of the fiducial element to determine said at least one of the dimensions of the rigid interconnections.

* * * * *